(12) United States Patent
Komori

(10) Patent No.: US 9,340,833 B2
(45) Date of Patent: May 17, 2016

(54) METHOD FOR ADJUSTING AMPLIFICATION EFFICIENCY OF TARGET POLYNUCLEOTIDE

(75) Inventor: Mariko Komori, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 389 days.

(21) Appl. No.: 13/098,415

(22) Filed: Apr. 30, 2011

(65) Prior Publication Data
US 2012/0202199 A1 Aug. 9, 2012

Related U.S. Application Data

(60) Provisional application No. 61/330,143, filed on Apr. 30, 2010.

(51) Int. Cl.
*C12Q 1/68* (2006.01)
(52) U.S. Cl.
CPC .............. *C12Q 1/6858* (2013.01); *C12Q 1/686* (2013.01)
(58) Field of Classification Search
None
See application file for complete search history.

(56) References Cited

U.S. PATENT DOCUMENTS 5,595,890 A 1/1997 Newton et al. ............... 435/91.2

FOREIGN PATENT DOCUMENTS

| DE | 19808534 | 9/1999 | ............... C12Q 1/68 |
|---|---|---|---|
| JP | 2853864 | 11/1998 | ............... C12Q 1/68 |
| JP | 2007-097492 A | 4/2007 | |
| JP | 2010-035532 | 2/2010 | ............... C12N 15/09 |
| WO | WO 97/16570 | 5/1997 | ............... C12Q 1/70 |
| WO | WO 2007/147063 | 12/2007 | ............... C12Q 1/68 |
| WO | WO 2008/061196 | 5/2008 | ............... C12Q 1/68 |

OTHER PUBLICATIONS

Tabone et al. (BMC Genomics, 2009, 10:580, p. 1-14).*
Myakishev et al. (Genome Research, 2001, vol. 11, p. 163-169).*
Katherisan et al. (NEJM, 2008, 358, p. 1240-9).*
Boekohldt et al. (Circulation, 2005, 111, p. 278-287).*
Watanabe et al. (Japanese Journal of Forensic Science and Technology, 2007, vol. 12, No. 1, p. 121-125).*
Tefferi et al. (J. Cell. Mol. Med., 2009, 13(2):215-237).*
The Extended European Search Report issued Aug. 16, 2011 in the corresponding European Patent Application No. 11164215.3.
Wang J. et al., "High-throughput SNP genotyping by single-tube PCR with $T_m$-shift primers", BioTechniques, Dec. 1, 2005, vol. 39, No. 6, pp. 885-893.
Casado-Diaz A. et al., "Individual single tube genotyping and DNA pooling by allele-specific PCR to uncover associations of polymorphisms with complex diseases", Clinica Chimica Acta, Aug. 17, 2006, vol. 376, pp. 155-162.
Cuppen E., "Genotyping by Allele-Specific Amplification (KASPar)", Cold Spring Harb. Protoc., Sep. 2007, vol. 9.
Navarro L. et al., "Single nucleoride polymorphism detection at the Hypothenemus hampei Rdl gene by allele-specific PCR amplification with $T_m$-shift primers", Pesticide Biochemistry and Physiology, Feb. 20, 2010, vol. 97, No. 3, pp. 204-208.
Office Action issued in corresponding European Patent Application No. 11164215.3 dated Aug. 19, 2013.
Myakishev et al., "High-Throughput SNP Genotyping by Allele-Specific PCR with Universal Energy-Transfer-Labeled Primers," Genome Research, 11: 163-169 (2001).
Troubleshooting Forum, "Molecular Biology Techniques Q&A," BioTechniques, 48: 101-103 (2010).
Watanabe et al., "Examination of the Primeres for Allele-Specific PCR Amplification," Japanese Journal of Forensic Science and Technology, 12: 121-125 (2007) (see partial English translation).
Office Action issued in corresponding Japanese Patent Application No. 2011-101037 dated Apr. 21, 2015 (see partial English translation).

\* cited by examiner

*Primary Examiner* — Stephanie K Mummert
(74) *Attorney, Agent, or Firm* — Morgan, Lewis & Bockius LLP

(57) ABSTRACT

Disclosed is a method for adjusting the amplification efficiency of a target polynucleotide in the amplification of the target polynucleotide by PCR using primers (i) to (iii) below, the method comprising adjusting the amplification efficiency of the target polynucleotide by changing the quantity ratio of the primers (i) to (iii) below:
  (i) a first primer which is able to be base-paired with the target polynucleotide;
  (ii) a second primer which is able to be base-paired with the target polynucleotide in competition with the first primer and from which extension reaction by PCR less occurs as compared to the first primer; and
  (iii) a third primer designed to allow for the amplification of the target polynucleotide in pairs with the first primer.

17 Claims, 10 Drawing Sheets

METHOD FOR ADJUSTING AMPLIFICATION EFFICIENCY OF TARGET POLYNUCLEOTIDE

RELATED APPLICATIONS

This application claims the benefit under 35 U.S.C. 119(e) of U.S. Provisional Application No. 61/330,143, filed Apr. 30, 2010, which is herein incorporated by reference in its entirety.

SEQUENCE LISTING SUBMISSION VIA EFS-WEB

A computer readable text file, entitled "068022-5024-SequenceListing.txt" created on or about Apr. 29, 2011 with a file size of about 4 kb contains the sequence listing for this application and is hereby incorporated by reference in its entirety.

TECHNICAL FIELD

The present invention relates to a method for adjusting the amplification efficiency of a target polynucleotide, a method for adjusting the detection efficiency of the target polynucleotide, and a method for detecting the target polynucleotide using the same. Furthermore, the present invention relates to a method for testing a disease and a method for making the diagnosis of the disease. Still furthermore, the present invention relates to a method for producing a primer set used for the amplification of a target polynucleotide and a method for producing a kit used for the detection of the target polynucleotide.

BACKGROUND ART

The allele-specific primer PCR (ASP-PCR) is a method used for the detection of mutations such as SNPs (single nucleotide polymorphisms). A typical allele-specific primer PCR uses a set of a primer that has a nucleotide corresponding to a mutated allele-specific nucleotide at the 3' end thereof, and a primer that, in pairs with the primer, amplifies a region comprising an SNP site to amplify specifically a target polynucleotide comprising a mutated allele, thereby detecting the mutated allele (Japanese Patent No. 2853864).

In the allele-specific primer PCR method as described above, however, it is necessary to set strict PCR conditions for amplifying specifically the target polynucleotide comprising the mutated allele, and thus, there has been a problem that it is difficult to achieve a high detection sensitivity (JP-A-2010-35532).

As a technique for solving such a problem, there is known a nucleic acid amplification method, which is an application technique of the typical allele-specific primer PCR. The method is characterized by that PCR reaction for a target nucleic acid is performed using (i) a first forward primer having a nucleotide sequence identical to a partial region comprising an SNP site of the target nucleic acid, except for having a wild-type nucleotide as the SNP site at only one of the second nucleotide and the third nucleotide from the 3' end, (ii) a second forward primer having a nucleotide sequence identical to the partial region comprising the SNP site of the target nucleic acid, except for having a mutated nucleotide as the SNP site at only one of the second nucleotide and the third nucleotide from the 3' end, and (iii) a reverse primer having a nucleotide sequence identical to a partial region on the 5' end side from the SNP site of a complementary chain of the target nucleic acid, the partial region not comprising a site corresponding to the SNP site (JP-A-2010-35532).

SUMMARY OF THE INVENTION

In the meantime, when the possibility of a disease associated with genetic mutation is measured by detecting the presence or absence of the genetic mutation, it is necessary for the purpose of obtaining significant detection results usable in the diagnosis of the disease to analyze the relationship between detection results of the mutation at various detection sensitivities and clinical findings on the mutation-associated disease, and thereby to establish detection sensitivity criteria for performing detection usable in the diagnosis.

As an approach for adjusting the detection sensitivity, it is usually conceivable to adjust the amplification efficiency of a target polynucleotide comprising a mutated allele by devising a primer design in accordance with mutation to be detected. Such an approach, however, requires repeating primer design, primer preparation, and amplification efficiency confirmation work, which often takes a great deal of work.

Therefore, it is an object of the present invention to provide a technique for easily adjusting the amplification efficiency of a target polynucleotide in a technique for amplifying the target polynucleotide.

As means for solving the above problem, the present invention provides a method for adjusting the amplification efficiency of a target polynucleotide in the amplification of the target polynucleotide by PCR using primers (i) to (iii) below, the method comprising adjusting the amplification efficiency of the target polynucleotide by changing the quantity ratio of the primers (i) to (iii) below.

The respective primers are described as follows.

(i) A first primer which is able to be base-paired with the target polynucleotide;

(ii) A second primer which is able to be base-paired with the target polynucleotide in competition with the first primer and from which extension reaction by PCR less occurs as compared to the first primer; and (iii) A third primer designed to allow for the amplification of the target polynucleotide in pairs with the first primer.

By the above method, the amplification efficiency of a target polynucleotide can be easily adjusted.

Examples of the quantity ratio of the primers include the quantity of the third primer with respect to the total quantity of the first primer and the second primer, and the quantity of the first primer with respect to the quantity of the second primer. By adjusting the quantity ratio of the primers as above, the amplification efficiency of the target polynucleotide can be easily adjusted.

In addition, the present invention provides a method for adjusting the detection efficiency (detection sensitivity) of a target polynucleotide in the detection of the target polynucleotide using an amplification product obtained by amplifying the target polynucleotide by PCR using the primers (i) to (iii), the method comprising adjusting the detection efficiency (detection sensitivity) of the target polynucleotide by using the amplification efficiency adjustment method according to the present invention.

By the above method, the detection efficiency of a target polynucleotide can be easily adjusted.

In addition, the present invention provides a method for detecting a target polynucleotide, the method comprising adjusting the detection efficiency of the target polynucleotide by the above method, performing PCR using the primers (i) to (iii) with a quantity ratio that achieves the adjusted detection efficiency, and detecting the target polynucleotide in an obtained PCR amplification product.

By the above detection method, a target polynucleotide can be easily detected at an appropriate detection sensitivity.

In addition, the present invention provides a method for testing the possibility of a disease due to the presence of a mutation, comprising detecting the presence or absence of a mutation in a gene derived from a subject by using the above detection method, wherein the presence of the mutation is indicative of increased risk of the disease.

By the above testing method the possibility of obtaining test results with small clinical significance can be decreased.

In addition, the present invention provides a method for predicting the efficacy of a medicine, the method comprising detecting the presence or absence of a mutation in a gene derived from a subject by using the above detection method, comparing an obtained detection result with the relationship between the presence or absence of the mutation and the efficacy of a specific medicine, and thereby predicting the efficacy of the specific medicine on the subject.

By the above method for predicting the efficacy of a medicine, the efficacy of a medicine can be predicted in medication, and thereby, effective medication is expected to be achieved.

Furthermore, the present invention provides a method for making the diagnosis of a disease, the method comprising making the diagnosis of the disease based on a test result obtained by the above testing method.

By the above diagnosis method, the possibility of obtaining inappropriate diagnosis results can be decreased.

In addition, the present invention provides a method for producing a primer set for amplifying or detecting a target polynucleotide by PCR. The production method comprises adjusting the amplification efficiency of a target polynucleotide by the above method and formulating the primers (i) to (iii) in a quantity ratio that achieves the adjusted amplification efficiency.

By the above production method, a primer set achieving arbitrary amplification efficiency and detection efficiency of a target polynucleotide can be produced.

In addition, the present invention provides a method for producing a detection kit for detecting a target polynucleotide using PCR. The production method comprises adjusting the amplification efficiency of the target polynucleotide by the above method and formulating the primers (i) to (iii) in a quantity ratio that achieves the adjusted amplification efficiency with a probe consisting of a sequence complementary to the target polynucleotide and labeled with a fluorescent dye at an end, in which fluorescence increases or decreases upon hybridization.

By the above production method, a detection kit achieving an arbitrary detection efficiency of a target polynucleotide can be easily produced.

In addition, the present invention provides a primer set comprising the above primers (i) to (iii), in which the quantity of the third primer with respect to the total quantity of the first primer and the second primer is more than 1 time by mole.

In addition, the present invention provides a primer set comprising the above primers (i) to (iii), in which the quantity of the third primer with respect to the total quantity of the first primer and the second primer is less than 1 time by mole.

The present invention allows for the easy adjustment of the amplification efficiency of a target polynucleotide. In addition, the present invention allows for the easy adjustment of the detection efficiency (detection sensitivity) of the target polynucleotide. By appropriately setting the detection sensitivity of the target polynucleotide, it is expected that measurement of the possibility of a disease associated with the target polynucleotide and the diagnosis of the disease can be made more accurately.

MODES FOR CARRYING OUT THE INVENTION

Figure 1:
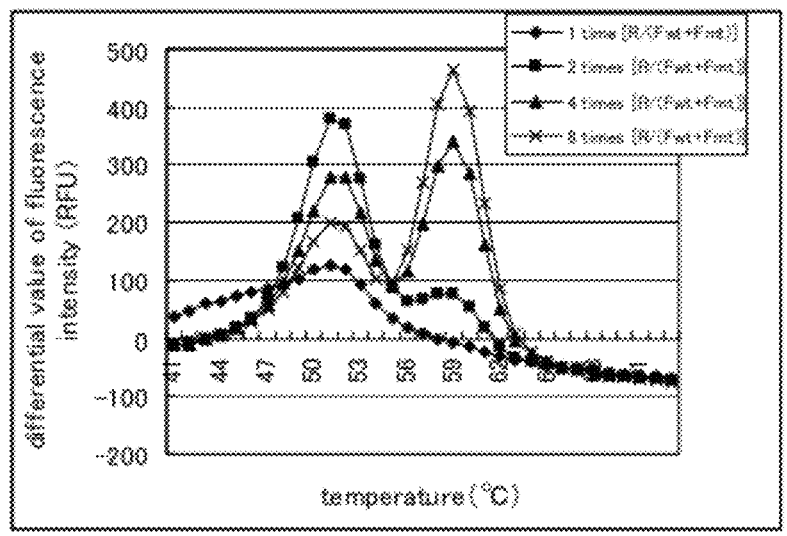
FIG. 1 is a view showing the influence of the quantity ratio between the total quantity of a first primer and a second primer and the quantity of a third primer on the detection sensitivity of a mutated plasmid (a target polynucleotide).

The present invention will be described by exemplifying preferred embodiments.

The first present invention relates to a method for adjusting the amplification efficiency of a target polynucleotide in the amplification of the target polynucleotide by PCR using primers (i) to (iii) below.

The present invention is characterized in that the amplification efficiency of the target polynucleotide is adjusted by changing the quantity ratio of the primers (i) to (iii) below.

The respective primers are as follows:
(i) a first primer which is able to be base-paired with the target polynucleotide;
(ii) a second primer which is able to be base-paired with the target polynucleotide in competition with the first primer and from which extension reaction by PCR less occurs as compared to the first primer; and
(iii) a third primer designed to allow for the amplification of the target polynucleotide in pairs with the first primer.

The term "target polynucleotide" is, for example, a polynucleotide containing a mutation. In this case, the mutation includes all of substitution, deletion, and insertion. An example of the mutation is a single base substitution. The present invention is suitable to adjust the amplification efficiency of a target polynucleotide comprising a mutated allele, in a polynucleotide comprising an SNP site.

Regarding the first primer, the phrase "be base-paired with the target polynucleotide" means that the first primer hybridizes with the target polynucleotide under the annealing conditions of PCR such that extension reaction occurs in PCR. However, as is obvious to those skilled in the art, the first primer does not need to be completely complementary to the sequence of a partial region of the target polynucleotide. The first primer may be base-paired with the sense chain of the target polynucleotide or base-paired with the antisense chain of the target polynucleotide. The first primer is designed in accordance with the sequence of the target polynucleotide.

There is mentioned that, in the first primer, usually, a nucleotide which is able to be base-paired with the target polynucleotide is arranged on the 3' end side of the primer, for example in a region of about the first to fifth positions from the 3' end (hereinafter may also be referred to as "3' end region"). Herein, when referring to "the first to fifth positions from the 3' end", the 3' end itself represents the first position. The design of such a primer can be appropriately performed by those skilled in the art.

For example, when the target polynucleotide is a mutated polynucleotide having a nucleotide substitution, the substituted nucleotide in the first primer may be arranged in the above-mentioned 3' end region thereof.

When the target polynucleotide comprises an SNP site, the first primer has a nucleotide corresponding to a first allele-specific nucleotide of the SNP site at any of the first to fifth positions from the 3' end, preferably at any of the first to third positions therefrom, more preferably at one of the first and the second positions therefrom, and most preferably at the 3' end, and can hybridize with a region comprising the SNP site. Herein, the phrase "nucleotide corresponding to a first allele-specific nucleotide" means a nucleotide complementary to the first allele-specific nucleotide when the first primer hybridizes with the sense chain, whereas it means a nucleotide identical to the first allele-specific nucleotide when the first primer hybridizes with the antisense chain. Additionally, "first allele-specific nucleotide" is defined by a combination with "second allele-specific nucleotide" that will be described below. For example, there may be mentioned a combination of a mutated nucleotide as the first allele-specific nucleotide and a wild-type nucleotide as the second allele-specific nucleotide or a reversed combination thereof, as well as a combination of a first mutated nucleotide as the first allele-specific nucleotide and a second mutate nucleotide as the second allele-specific nucleotide.

Furthermore, even when the target polynucleotide is a mutated polynucleotide having a nucleotide insertion, the first primer can be designed in the same manner as the case of the above-described substitution, in which a nucleotide which is able to be base-paired with the inserted nucleotide may be arranged in the 3' end region.

In addition, when the target polynucleotide is a mutated polynucleotide having a nucleotide deletion, a nucleotide which is able to be base-paired with a region comprising positions upstream and downstream of the deletion site may be arranged in the 3' end region.

Regarding the second primer, the phrase "be base-paired with the target polynucleotide in competition with the first primer" means that the second primer hybridizes with the region of the target polynucleotide with which the first primer hybridizes in competition with the first primer under the annealing conditions of PCR. Accordingly, the second primer has a homology of usually about from 60 to 95% to the first primer. Herein, from the second primer, extension reaction by PCR less occurs as compared to the first primer. Such a second primer can be designed in consideration of the sequence of the target polynucleotide and the sequence of the first primer. In general, there is mentioned that a nucleotide which is unable to be base-paired with the target polynucleotide is arranged in the direction of PCR extension (on the 3' end side). Additionally, there is mentioned that the sequence is designed such that the Tm value of the second primer is lower than the Tm value of the first primer. The design of such a primer can be appropriately performed by those skilled in the art. Usually, a nucleotide which is unable to be base-paired with the target polynucleotide is arranged on the 3' end side of the primer, for example in the region of the first to fifth positions from the 3' end (hereinafter may be referred to as "3' end region"). For example, when the target polynucleotide is a polynucleotide comprising a mutation, there is mentioned that, in the second primer, not a nucleotide which is able to be base-paired with the sequence of a mutated part but a nucleotide which is able to be base-paired with a wild-type sequence is arranged in the 3' end region.

When the target polynucleotide comprises an SNP site, the second primer has a nucleotide corresponding to a second allele-specific nucleotide of the SNP site at any of the first to fifth positions from the 3' end, preferably at any of the first to third positions therefrom, more preferably at one of the first and the second positions therefrom, and most preferably at the 3' end, and can hybridize with a region comprising the SNP site.

The third primer is designed to allow for the amplification of the target polynucleotide in pairs with the first primer. That is, the third primer is designed to be base-paired with the complementary chain of a polynucleotide chain with which the first primer is able to be base-paired in a downstream region in a direction of extension by the first primer.

The length and the Tm value of each primer can be appropriately designed in accordance with the sequence of the target polynucleotide and usually are 10 to 40 mer and 40 to 70° C., preferably 15 to 30 mer and 50 to 60° C. The Tm values are those calculated by the nearest neighbor method.

In an embodiment of the present invention, the Tm value of the first primer is higher than the Tm value of the second primer. The Tm values are those calculated by the nearest neighbor method. In this case, the difference between the Tm value of the first primer and the Tm value of the second primer is preferably 0.1 to 10° C., and more preferably 0.5 to 5° C. When the Tm value of the first primer is higher than that of the second primer, the method according to the present invention easily increases the amplification efficiency of the target polynucleotide.

The Tm value can be calculated from CG content and the number of nucleotides. The easiest method for designing the primers such that the Tm value of the first primer is higher than that of the second primer is to make the length of the first primer longer than that of the second primer. For example, there may be mentioned a method in which the length of the first primer is increased by about 1 to 10 nucleotides compared to the length of the second primer, and preferably by about 2 to 5 nucleotides compared thereto.

In addition, it is preferable to add oligonucleotides having sequences different from each other consisting of several nucleotides at the 5' end of the first primer and the 5' end of the second primer respectively. The added sequences have a length of usually about 1 to 20 nucleotides, and a length of preferably about 3 to 10 nucleotides. The reason for this is to reduce the possibility that the first primer hybridizes with a polynucleotide different from the target polynucleotide and thereby amplification occurs using a nucleotide other than the target polynucleotide as a template, and thereby to ensure the adjustment of the amplification efficiency of the target polynucleotide.

In an embodiment of the first present invention, when the Tm value of the first primer is higher than that of the second primer, the amplification efficiency of the target polynucleotide can be increased by increasing the quantity of the third primer with respect to the total quantity of the first primer and the second primer.

Conversely, by decreasing the quantity of the third primer with respect to the total quantity of the first primer and the second primer, the amplification efficiency of the target polynucleotide can be decreased.

That is, the amplification efficiency of the target polynucleotide can be increased or decreased by changing the primer quantity ratio by the above methods.

In the embodiment, specifically by making the quantity of the third primer with respect to the total quantity of the first primer and the second primer more than 1 time by mole, the amplification efficiency of the target polynucleotide can be increased. In a conventional PCR method (for example, JP-A-2010-35532) having the same system as that of the present invention, the quantity ratio between a forward primer and a reverse primer has been a mole ratio of about 1:1. Thus, by making the quantity of the third primer with the total quantity of the first primer and the second primer more than 1 time by mole, the amplification efficiency of the target polynucleotide can be increased as compared to the amplification efficiency of the target polynucleotide in the conventional PCR method.

In addition, the amplification efficiency of the target polynucleotide can be further increased by making the quantity of the third primer with respect to the total quantity of the first primer and the second primer more than 2 times by mole. Additionally, as is clear from the Example, the amplification efficiency of the target polynucleotide can be further increased by making the quantity of the third primer with respect to the total quantity of the first primer and the second primer more than 4 times by mole, and furthermore, more than 8 times by mole.

In addition, specifically, by making the quantity of the third primer with respect to the total quantity of the first primer and the second primer less than 1 time by mole, the amplification efficiency of the target polynucleotide can be decreased. In the conventional PCR method (for example, JP-A-2010-35532) having the same system as that of the present invention, the quantity ratio between the forward primer and the reverse primer has been the mole ratio of about 1:1. Thus, by making the quantity of the third primer with the total quantity of the first primer and the second primer less than 1 time by mole, the amplification efficiency of the target polynucleotide can be decreased as compared to the amplification efficiency of the target polynucleotide in the conventional PCR method.

In addition, the amplification efficiency of the target polynucleotide can be further decreased by making the quantity of the third primer with respect to the total quantity of the first primer and the second primer less than 0.5 times by mole. Additionally, the amplification efficiency of the target polynucleotide can be further decreased by making the quantity of the third primer with respect to the total quantity of the first primer and the second primer less than 0.25 times by mole, and furthermore, less than 0.125 times by mole.

In another embodiment of the first present invention, by increasing the quantity of the first primer with respect to the quantity of the second primer, the amplification efficiency of the target polynucleotide can be increased.

Conversely, by decreasing the quantity of the first primer with respect to the quantity of the second primer, the amplification efficiency of the target polynucleotide can be decreased.

That is, by changing the quantity ratio of the primers by the above methods, the amplification efficiency of the target polynucleotide can be increased or decreased.

In the embodiment, specifically, by making the quantity of the first primer with respect to the quantity of the second primer more than 1 time by mole, the amplification efficiency of the target polynucleotide can be increased.

In the conventional PCR method (for example, JP-A-2010-35532) having the same system as that of the present invention, the quantity ratio between the first primer and the second primer has been the mole ratio of about 1:1. Thus, by making the quantity of the first primer with respect to the quantity of the second primer more than 1 time by mole, the amplification efficiency of the target polynucleotide can be increased as compared to the amplification efficiency of the target polynucleotide in the conventional PCR method.

In addition, the amplification efficiency of the target polynucleotide can be further increased by making the quantity of the first primer with respect to the quantity of the second primer more than 2 times by mole.

The upper limit of the quantity of the first primer with respect to the quantity of the second primer is preferably 4 times by mole.

In another preferable embodiment, the embodiment in which the quantity of the first primer with respect to the quantity of the second primer is changed is combined with the embodiment in which the quantity of the third primer with respect to the total quantity of the first primer and the second primer is changed.

By adjusting the amplification efficiency of the target polynucleotide according to the above methods, the primer quantity ratio that achieves an amplification efficiency in accordance with the purpose of amplification of the target polynucleotide can be determined. That is, the present invention also provides a method for determining the primer quantity ratio in the amplification of the target polynucleotide by PCR using the primers (i) to (iii) described above.

By performing PCR using the primers of the quantity ratio thus determined, the amplification efficiency in accordance with the purpose of the target polynucleotide can be achieved.

That is, the present invention provides a method for amplifying a target polynucleotide, the method comprising adjusting the amplification efficiency of the target polynucleotide by the above method and performing PCR using the primers (i) to (iii) of the quantity ratio that achieves the adjusted amplification efficiency.

The first present invention described above allows for the adjustment of the amplification efficiency of a target polynucleotide in PCR. In addition, by adjusting the amplification efficiency of the target polynucleotide using the first present invention, the detection efficiency (detection sensitivity) of the target polynucleotide can be adjusted.

That is, the second present invention is a method for adjusting the detection efficiency (detection sensitivity) of a target polynucleotide in the detection of the target polynucleotide using an amplification product obtained by amplifying the target polynucleotide by PCR using the primers (i) to (iii), the method comprising adjusting the detection efficiency (detection sensitivity) of the target polynucleotide by using the amplification efficiency adjustment method according to the present invention.

An embodiment of the method for adjusting the quantity ratio of the primers is the same as described in the first present invention. That is, there is a relationship in which the detection sensitivity of the target polynucleotide becomes higher as the amplification efficiency of the target polynucleotide is increased by the adjustment of the quantity ratio of the primers described above.

By adjusting the detection efficiency (detection sensitivity) of the target polynucleotide according to the above method, the primer quantity ratio that achieves a detection efficiency in accordance with the purpose of detection of the target polynucleotide can be determined. That is, the present invention also provides a method for determining the primer quantity ratio in the detection of the target polynucleotide by PCR using the above primers (i) to (iii).

Detection efficiency in accordance with purposes can be achieved by performing PCR using the primers of a quantity ratio thus determined and detecting the target polynucleotide comprised in an obtained PCR amplification product.

That is, the present invention provides a method for detecting a target polynucleotide, the method comprising adjusting the detection efficiency of the target polynucleotide by the above method, performing PCR using the primers (i) to (iii) of a quantity ratio achieving the adjusted detection efficiency, and detecting the target polynucleotide comprised in an obtained PCR amplification product.

The method for detecting target polynucleotide may be a known method. Examples of the known method include melting curve analysis (Tm analysis), sequencing, and electrophoresis. Among them, detection by melting curve analysis (Tm analysis) is preferable. The reason for this is that when Tm analysis is performed, a reaction solution containing an amplification product can be subjected to the analysis, as it is, without particularly processing the amplification product of a target polynucleotide. Additionally, it is easy since an apparatus for sequentially performing amplification and Tm analysis (see Examples) is also in practical use.

The Tm analysis can use a probe consisting of a sequence complementary to a target polynucleotide and labeled with a fluorescent dye at an end, in which the fluorescence increases or decreases when the probe hybridizes to the target polynucleotide to form double strands; SYBR Green (SYBR: registered trademark) intercalating with double-stranded DNA; or HybProbe in which fluorescence resonance energy transfer (FRET) occurs between two kinds of adjacent probes. As the probe labeled with a fluorescent dye at an end, in which the fluorescence decreases when the probe hybridizes to the target polynucleotide to form double strands, there may be mentioned a method using a fluorescent DNA probe using a fluorescent dye in which fluorescence quenching occurs when a guanine nucleotide of DNA comes close to the dye, which is the so-called QProbe (registered trademark) (//unit.aist.go.jp/brf/ci/research_result/aist_today/vol08_02_p18_p19.pdf, and //www.wipo.int/pctdb/ja/wo.jsp?WO=2008117782&IA=JP2008055469&DISPLAY=FT). The fluorescent dye used for such a probe is known and a method for preparing the probe is also known. Herein, regarding the "sequence complementary to the target polynucleotide", it is only necessary for the sequence to be complementary in an extent capable of hybridizing to the target polynucleotide under normal conditions in the above detection method, so that the sequence does not need to be completely complementary thereto.

In addition, examples of the fluorescence dye used for the probe in which the fluorescence decreases upon the formation of double strands include Pacific Blue, TAMRA, and BODIPY FL from Invitrogen Ltd. The length of the probe can be appropriately designed in accordance with a polynucleotide that will be a detection target and is usually about 10 to 40 mer.

The Tm analysis can be performed by measuring fluorescence intensity detected when gradually increasing the temperature of a reaction solution. The measurement of the fluorescence intensity is performed by measuring light having an emission wavelength using excitation light having a wavelength in accordance with a fluorescent dye to be used. Temperature increase speed in the Tm analysis is usually from 0.1 to 1° C. per 5 seconds. Composition of the reaction solution in the Tm analysis is not particularly limited as long as it allows for the hybridization of the probe with a polynucleotide having a sequence complementary to its nucleotide sequence. The concentration of monovalent positive ions is usually from 1.5 to 50 mM and pH is from 7 to 9. Reaction solution for an amplification method using DNA polymerase, such as PCR, usually satisfies the above conditions, and thus the reaction solution used for amplification can be used as it is in the Tm analysis.

Then, based on the results of the Tm analysis, the target polynucleotide is detected. The detection of the target polynucleotide based on the Tm analysis results can be performed by a usual method. In the present invention, "detection" means a concept including, in addition to the detection of the presence or absence of a target polynucleotide, quantitative determination of the target polynucleotide in a sample, and the measurement of the ratio between the target polynucleotide and the other polynucleotides in a sample.

In addition, using the above detection method allows for the detection of the presence or absence of a mutation in a gene derived from a subject. That is, the third present invention is a method for testing the possibility of a disease due to the presence of a mutation, comprising detecting the presence or absence of a mutation in a gene derived from a subject by using the above detection method, wherein the presence of the mutation is indicative of increased risk of the disease. In the third present invention, by comparing a detection result obtained by the above detection method with the criterion that the subject may have the disease due to the presence of the mutation in the case where the mutation is detected, the possibility of the disease due to the presence of the mutation can be tested. Additionally, the present invention also provides a method for making the diagnosis of the disease based on the above testing result.

The fourth present invention is a method for predicting the efficacy of a medicine, the method comprising comparing a detection result obtained using the above detection method with the relationship between the presence or absence of the mutation and the efficacy of a specific medicine, and thereby predicting the efficacy of the specific medicine on the subject. In other words, in the case where the relationship between a specific mutation and the efficacy of a specific medicine is known, detecting the presence or absence of the specific mutation and referring to the above known relationship allows for the prediction of the efficacy of the specific medicine.

For example, it is known that Gefitinib, which is a molecular target drug, exhibits a high response rate when there is a specific mutation in the EGFR gene (such as L858R mutation of exon 21). It is also known that Cetuximab, which is a molecular target drug, is not effective when there is a mutation in the codon 12 or 13 of the kras gene or there is the V600E mutation in the braf gene. In other words, by detecting the above mutation in the EGFR gene using the detection method according to the present invention, the efficacy of Gefitinib on the subject can be predicted. Additionally, by detecting the above mutation in the kras gene or the braf gene using the detection method according to the present invention, the efficacy of Cetuximab on the subject can be predicted.

In addition, the present invention provides a method for producing a primer set used in a method for amplifying a target polynucleotide using the above-described primers (i) to (iii).

That is, the fifth present invention is a method for producing a primer set, the method comprising adjusting the amplification efficiency of a target polynucleotide using the above-described first present invention and formulating the primers in a quantity ratio that achieves the adjusted amplification efficiency.

The above production method allows for the provision of a primer set suitable for the amplification and detection of a target polynucleotide.

Herein, examples of "formulating" include an embodiment in which the primers are mixed and an embodiment in which the primers are separately included so that the primers can be mixed together in use.

In addition, the present invention provides a method for designing a primer set used in the method for amplifying a target polynucleotide using the above-described primers (i) to (iii).

That is, another embodiment of the present invention is a method for designing a primer set by adjusting the amplification efficiency of a target polynucleotide by using the above-described first present invention and determining a primer quantity ratio that achieves the adjusted amplification efficiency.

Such a designing method allows for the easy designing of a primer set suitable for the amplification and detection of a target polynucleotide.

A primer set according to the sixth present invention can have the following structure, for example. The primer set is used for the amplification and detection of a target polynucleotide.

A primer set comprising primers (i) to (iii) below, in which the quantity of a third primer with respect to the total quantity of a first primer and a second primer is more than 1 time by mole:

(i) the first primer which is able to be base-paired with a target polynucleotide;

(ii) the second primer which is able to be base-paired with the target polynucleotide in competition with the first primer and from which extension reaction by PCR less occurs as compared to the first primer; and (iii) the third primer designed to allow for the amplification of the target polynucleotide in pairs with the first primer.

The above primer set is used, for example, for the amplification and detection of a target polynucleotide comprising an SNP site. In this case, the first primer has a nucleotide corresponding to a first allele-specific nucleotide of the SNP site at any of the first to fifth positions from the 3' end, and the second primer has a nucleotide corresponding to a second allele-specific nucleotide of the SNP site at any of the first to fifth positions from the 3' end.

Other preferable embodiments of the respective primers are the same as those described in the first present invention. In an embodiment, the Tm value of the first primer is higher than the Tm value of the second primer.

The quantity of the third primer with respect to the total quantity of the first primer and the second primer is preferably more than 2 times by mole, more preferably more than 4 times by mole, and still more preferably more than 8 times by mole.

In addition, the present invention also provides primer sets each comprising the above primers (i) to (iii), in which the quantity of the third primer with respect to the total quantity of the first primer and the second primer is less than 1 time by mole, less than 0.5 times by mole, less than 0.25 times by mole, less than 0.125 times by mole, or the like.

As another embodiment of the primer set according to the sixth present invention, for example, there may be mentioned a primer set as follows:

A primer set comprising primers (i) and (ii) below, in which the quantity of the first primer with respect to the quantity of the second primer is more than 1 time by mole, (i) the first primer which is able to be base-paired with the target polynucleotide; and (ii) the second primer which is able to be base-paired with the target polynucleotide in competition with the first primer and from which extension reaction by PCR less occurs as compared to the first primer.

The quantity of the first primer with respect to the quantity of the second primer is preferably more than 2 times by mole. The upper limit of the quantity of the first primer with respect to the quantity of the second primer is preferably 4 times by mole.

Furthermore, the present invention provides a method for producing a detection kit used in the method for detecting a target polynucleotide in an amplification product by amplifying the target polynucleotide using the above-described primers (i) to (iii).

The detection kit production method comprises adjusting the amplification efficiency of a target polynucleotide using the above-described first present invention and formulating the primers with a quantity ratio that achieves the adjusted amplification efficiency with a probe consisting of a sequence complementary to the target polynucleotide and labeled with a fluorescent dye at an end, in which the fluorescence increases or decreases upon hybridization. Such a probe is the same as described in the first present invention.

Furthermore, the present invention also provides a detection kit in which the primer set according to the sixth invention is combined with the above probe.

EXAMPLES

Example 1

SEQ ID NO:1 is a partial sequence of a JAK2 gene sequence. SEQ ID NO:1 corresponds to the sequence from the 88381st to 88680th in GenBank Accession No. NG_009904. A DNA fragment consisting of the sequence from the 18th to 237th in the nucleotide sequence shown in SEQ ID NO:1 was inserted into the EcoRV site of pT7Blue T-vector by TA cloning and was linearized with EcoR1. The obtained product was defined as a wild-type plasmid (JAK2 Wt plasmid). In addition, the same processing was performed on a DNA fragment consisting of a sequence in which the 147th guanine (G) in the nucleotide sequence shown in SEQ ID NO:1 was replaced with thymine (T), and the obtained product was defined as a mutated plasmid (JAK2 V617F plasmid). The sample was prepared by mixing the JAK2 Wt plasmid and the JAK2 V617F plasmid in a ratio of 99:1.

By using 50 µl of the PCR reaction solution containing $10^4$ copies of the sample and each component of the PCR reaction shown in Table 1 at the concentrations described below, PCR and Tm analysis were performed by using a full-automated SNP analyzer (trade name: i-densy (registered trademark) from Arkray Inc.). As primers, the wild-type JAK2 primer Fwt (the 3' end is a wild-type nucleotide; SEQ ID NO:2), the mutated JAK2 primer Fmt (the 3' end is a mutated nucleotide; SEQ ID NO:3), and the JAK2 primer R (SEQ ID NO:4) in pairs with them were used. In addition, as a probe, the probe (SEQ ID NO:5) labeled with a fluorescent dye (TAMRA) at the 3' end, in which the fluorescence decreases upon the formation of double strands, was used. Table 2 shows the sequences and the lengths of the primers and the probe. In Table 2, the sequences consisting of nucleotides indicated by capital letters on the 5' ends of the JAK2 primer Fwt and the JAK2 primer Fmt are additional sequences for the inhibition of false positive results.

By changing the concentration of the JAK2 primer R as shown in Table 3, the quantity ratio between the total quantity of the JAK2 primer Fwt and the JAK2 primer Fmt and the quantity of the JAK2 primer R was changed, thereby testing influence of the quantity ratio on the detection sensitivity of the mutated plasmid.

Table 4 shows the conditions for the PCR and the Tm analysis. Additionally, excitation wavelength and detection wavelength in the Tm analysis were 520 to 555 nm and 585 to 700 nm, respectively.

TABLE 1

In 50 µl of the PCR reaction solution:

1 × reaction buffer
1.25 U Taq polymerase
1.5 mmol/L MgCl$_2$
0.2 mmol/L dNTP
0.25 µmol/L JAK2 primer Fwt (Table 2)
0.25 µmol/L JAK2 primer Fmt (Table 2)
0.2 µmol/L JAK2 mt probe (Table 2)

*The concentration of JAK2 primer R (Table 2) is referred to in Table 3.

TABLE 2

| JAK2 primer Fwt | 5'-TGCTCatttggttttaaattatggagtatgtG-3' | 32 mer | Tm: 58.21° C. |
| JAK2 primer Fmt | 5'-GTCTGgcatttggttttaaattatggagtatgtT-3' | 34 mer | Tm: 59.21° C. |
| JAK2 primer R | 5'-gctctgagaaaggcattagaaagcctg-3' | 27 mer | |

TABLE 2-continued

| | | |
|---|---|---|
| JAK2 mt probe | 5'-agtatgtTtctgtggagac-(TAMRA)-3' | 19 mer |

Tm represents values calculated by the Nearest Neighbor Method (primer conc.: 250 nM; Na⁺ conc.: 50 mM) in the URL: //www.m-neko.net/tm_calc/.

TABLE 3

| primer quantity ratio: R/(Fwt + Fmt) | 1 time by mole | 2 times by mole | 4 times by mole | 8 times by mole |
|---|---|---|---|---|
| Concentration of JAK2 primer R in PCR reaction solution (μmol/L) | 0.5 | 1 | 2 | 4 |

TABLE 4

PCR conditions/Tm analysis conditions

95° C., 60 seconds
↓
(95° C., 1 second → 60° C., 15 seconds) × 50 cycles
↓
95° C., 1 second
↓
40° C., 60 seconds
↓
Tm analysis: 40° C. → 75° C., 1° C./3 seconds FIG. 1 shows the results of the PCR and the Tm analysis. In FIG. 1, the vertical axis represents the differential values of fluorescence intensity (Relative Fluorescence Units (RFU)) and the horizontal axis represents temperatures (° C.). The peak seen at around 51° C. indicates a peak resulted from the presence of the wild-type plasmid, and the peak seen at around 59° C. indicates a peak resulted from the presence of the mutated plasmid.

As shown in FIG. 1, the peak resulted from the presence of the mutated plasmid became larger, as the quantity of the JAK2 primer R with respect to the total quantity of the JAK2 primer Fwt and the JAK2 primer Fmt (R/(Fwt+Fmt)) was increased to 2 times by mole, 4 times by mole, and 8 times by mole.

This indicated the regularity that as the value of (R/(Fwt+Fmt)) becomes larger, the amplification efficiency of the mutated plasmid increases.

Example 2

SEQ ID NO:6 is a partial sequence of an abl gene sequence. SEQ ID NO:6 corresponds to the sequence from the 158941st to 159060th in GenBank Accession No. NG_012034. A DNA fragment consisting of the sequence of at least from the 19th to 100th in the nucleotide sequence shown in SEQ ID NO:6 was inserted into the EcoRV site of pT7Blue T-vector by TA cloning and was linearized with KpnI. The obtained product was defined as a wild-type plasmid (abl Wt plasmid). In addition, the same processing was performed on a DNA fragment consisting of a sequence in which the 77th cytosine (C) in the nucleotide sequence shown in SEQ ID NO:6 was replaced with thymine (T), and the obtained product was defined as a mutated plasmid (abl C944T plasmid). The sample was prepared by mixing the abl Wt plasmid and the abl C944T plasmid in the ratio of 99:1.

By using 50 μl of the PCR reaction solution containing $10^4$ copies of the sample and each component of the PCR reaction shown in Table 5 at the concentrations described below, PCR and Tm analysis were performed by using the full-automated SNP analyzer (trade name: i-densy (registered trademark) from Arkray Inc.). As primers, the wild-type abl primer Rwt (the 3' end is a wild-type nucleotide; SEQ ID NO:8), the mutated abl primer Rmt (the 3' end is a mutated nucleotide; SEQ ID NO:9), and the abl primer F (SEQ ID No:7) in pairs with them were used. In addition, as a probe, the probe (SEQ ID NO:10) labeled with a fluorescent dye (BODIPY FL) at the 5' end and phosphorylated at the 3' end (indicated by "P" in Table 6), in which the fluorescence decreases upon the formation of double strands, was used. Table 6 shows the sequences and the lengths of the primers and the probe.

By changing the concentration of the abl primer F as shown in Table 7, the quantity ratio between the total quantity of the abl primer Rwt and the abl primer Rmt and the quantity of the abl primer F was changed, thereby testing influence of the quantity ratio on the detection sensitivity of the mutated plasmid.

Table 8 shows the conditions for the PCR and the Tm analysis. Additionally, excitation wavelength and detection wavelength in the Tm analysis were 420 to 485 nm and 520 to 555 nm, respectively.

TABLE 5

In 50 μl of the PCR reaction solution:

1 × reaction buffer
1.25 U Taq polymerase
1.5 mmol/L MgCl₂
0.2 mmol/L dNTP
0.25 μmol/L abl primer Rwt (Table 6)
0.25 μmol/L abl primer Rmt (Table 6)
0.2 μmol/L abl mt probe (Table 6)

*The concentration of abl primer F (Table 6) is referred to in Table 7.

TABLE 6

| abl primer F | 5'-GGACGGACGGACCgtcctcgttgtcttgttggc-3' | (SEQ ID NO: 7) | 33 mer | |
| abl primer Rwt | 5'-CTACGttcccgtaggtcatgaactcaG-3' | (SEQ ID NO: 8) | 27 mer | Tm: 60.52° C. |
| abl primer | 5'-TGCTCaggttcccgtaggtcatgaactcaA-3' | (SEQ ID NO: 9) | 30 mer | Tm: 63.63° C. |

TABLE 6-continued

Rmt

| | | |
|---|---|---|
| abl mt probe | 5'-(BODIPY FL)-ctcaAtgatgatatagaacg-P-3' (SEQ ID NO: 10) | 20 mer |

Tm represents values calculated by the Nearest Neighbor Method (primer conc.: 250 nM; Na⁺ conc.: 50 mM) in the URL: //www.m-neko.net/tm_calc/.

TABLE 7

| primer quantity ratio: F/(Rwt + Rmt) | 4 times by mole | 8 times by mole |
|---|---|---|
| Concentration of abl primer F in PCR reaction solution (μmol/L) | 2 | 4 |

TABLE 8

PCR conditions/Tm analysis conditions

Figure 2:
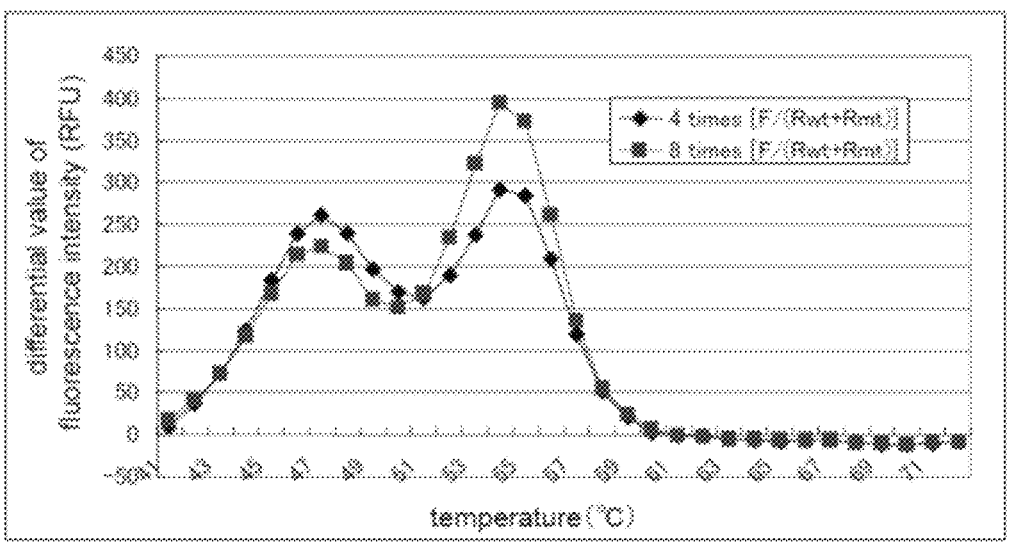
FIG. 2 is a view showing the influence of the quantity ratio between the total quantity of a first primer and a second primer and the quantity of a third primer on the detection sensitivity of a mutated plasmid (a target polynucleotide).

95° C., 60 seconds
↓
(95° C., 1 second → 65° C., 15 seconds) × 50 cycles
↓
95° C., 1 second
↓
40° C., 60 seconds
↓
Tm analysis: 40° C. → 75° C., 1° C./3 seconds FIG. 2 shows the results of the PCR and the Tm analysis. In FIG. 2, the vertical axis represents the differential values of fluorescence intensity (Relative Fluorescence Units (RFU)) and the horizontal axis represents temperatures (° C.). The peak seen at around 47° C. indicates a peak resulted from the presence of the wild-type plasmid, and the peak seen at around 54° C. indicates a peak resulted from the presence of the mutated plasmid.

As shown in FIG. 2, the peak resulted from the presence of the mutated plasmid became larger, as the quantity of the abl primer F with respect to the total quantity of the abl primer Rwt and the abl primer Rmt (F/(Rwt+Rmt)) was increased to 4 times by mole and 8 times by mole.

This indicated the regularity that as the value of (F/(Rwt+Rmt)) becomes larger, the amplification efficiency of the mutated plasmid increases.

The results obtained in Example 1 and Example 2 showed that changing the quantity ratio between a primer having an allele-specific nucleotide and an allele-nonspecific primer allows for an increase in the amplification efficiency of a DNA having a particular allele-specific nucleotide.

Example 3

SEQ ID NO:11 is a partial sequence of a kit gene sequence. SEQ ID NO:11 corresponds to the sequence from the 75001st to 75360th in GenBank Accession No. NG_007456. A DNA fragment consisting of the sequence from the 59th to 358th in the nucleotide sequence shown in SEQ ID NO:11 was inserted into the EcoRV site of pT7Blue T-vector by TA cloning and was linearized with EcoR1. The obtained product was defined as a wild-type plasmid (kit Wt plasmid). In addition, the same processing was performed on a DNA fragment consisting of a sequence in which the 228th adenine (A) in the nucleotide sequence shown in SEQ ID NO:11 was replaced with thymine (T), and the obtained product was defined as a mutated plasmid (kit D617V plasmid). The sample was prepared by mixing the kit Wt plasmid and the kit D617V plasmid in the ratio of 99:1.

By using 50 μl of the PCR reaction solution containing $10^4$ copies of the sample and each component of the PCR reaction shown in Table 9 at the concentrations described below, PCR and Tm analysis were performed by using the full-automated SNP analyzer (trade name: i-densy (registered trademark) from Arkray Inc.). As primers, the wild-type kit primer Fwt (the 3' end is a wild-type nucleotide; SEQ ID NO:12), the mutated kit primer Fmt (the 3' end is a mutated nucleotide; SEQ ID NO:13), and the kit primer R (SEQ ID NO:14) in pairs with them were used. In addition, as a probe, the probe (SEQ ID NO:15) labeled with the fluorescent dye (TAMRA) at the 5' end and phosphorylated at the 3' end, in which the fluorescence decreases upon the formation of double strands, was used. Table 10 shows the sequences and the lengths of the primers and the probe.

By changing the concentration of the kit primer Fwt as shown in Table 11, the quantity ratio between the kit primer Fwt and the kit primer Fmt was changed, thereby testing influence of the quantity ratio on the detection sensitivity of the mutated plasmid.

Table 12 shows the conditions for the PCR and the Tm analysis. Additionally, excitation wavelength and detection wavelength in the Tm analysis were 520 to 555 nm and 585 to 700 nm, respectively.

TABLE 9

In 50 μl of the PCR reaction solution:

1 × reaction buffer
1.25 U Taq polymerase
1.5 mmol/L MgCl₂
0.2 mmol/L dNTP
0.25 μmol/L kit primer Fmt (Table 10)
1 μmol/L kit primer R (Table 10)
0.2 μmol/L kit mt probe (Table 10)

*The concentration of kit primer Fwt (Table 10) is referred to in Table 11.

TABLE 10

| | | | |
|---|---|---|---|
| kit primer Fwt | 5'-attttggtctagccagagA-3' | (SEQ ID NO: 12) | 19 mer |
| kit primer Fmt | 5'-tgattttggtctagccagagT-3' | (SEQ ID NO: 13) | 21 mer |
| kit primer R | 5'-aaatcctttgcaggactgtc-3' | (SEQ ID NO: 14) | 20 mer |
| kit mt probe | 5'-(TAMRA)-ccagagTcatcaagaatg-P-3' | (SEQ ID NO: 15) | 18 mer |

TABLE 11

| primer quantity ratio: Fwt/Fmt | 1 time by mole | 2 times by mole |
|---|---|---|
| Concentration of kit primer Fwt in PCR reaction solution (μmol/L) | 0.25 | 0.5 |

TABLE 12

PCR conditions/Tm analysis conditions

Figure 3:
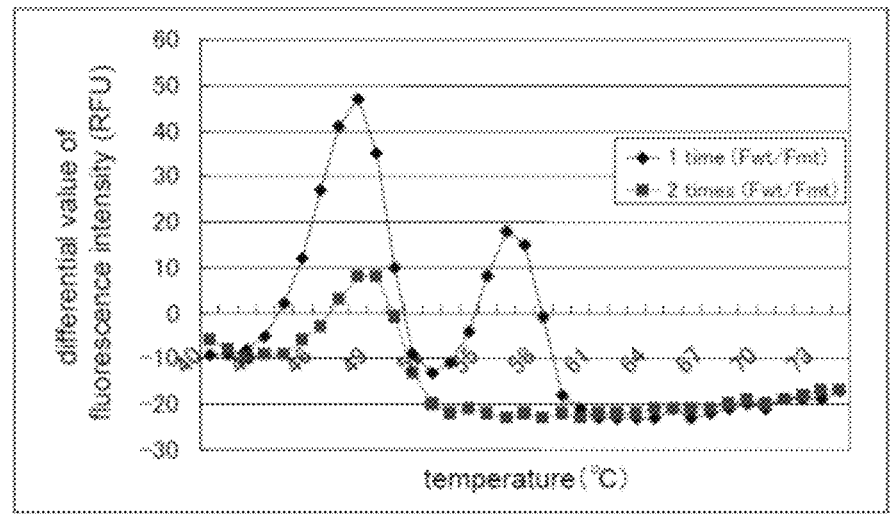
FIG. 3 is a view showing the influence of the quantity ratio between a first primer and a second primer on the detection sensitivity of a mutated plasmid (a target polynucleotide).

95° C., 60 seconds
↓
(95° C., 1 second → 61° C., 15 seconds) × 50 cycles
↓
95° C., 1 second
↓
40° C., 60 seconds
↓
Tm analysis: 40° C. → 75° C., 1° C./3 seconds FIG. 3 shows the results of the PCR and the Tm analysis. In FIG. 3, the vertical axis represents the differential values of fluorescence intensity (Relative Fluorescence Units (RFU)) and the horizontal axis represents temperatures (° C.). The peak seen at around 48° C. indicates a peak resulted from the presence of the wild-type plasmid, and the peak seen at around 56° C. indicates a peak resulted from the presence of the mutated plasmid.

As shown in FIG. 3, the peak resulted from the presence of the mutated plasmid became larger, as the quantity of the kit primer Fwt with respect to the quantity of the kit primer Fmt (Fwt/Fmt) was decreased from 2 times by mole to 1 time by mole.

This indicated the regularity that as the value of (Fwt/Fmt) becomes smaller, the amplification efficiency of the mutated plasmid increases.

Example 4

The sample was prepared by mixing the JAK2 Wt plasmid and the JAK2 V617F plasmid prepared in Example 1 in the ratio of 99:1, and the following test was performed using the various primers and the probe shown in Table 2.

By using 50 μl of the PCR reaction solution containing 10⁴ copies of the sample and each component of the PCR reaction shown in Table 13 at the concentrations described below, PCR and Tm analysis were performed by using the full-automated SNP analyzer (trade name: i-densy (registered trademark) from Arkray Inc.).

By changing the concentration of the JAK2 primer Fmt as shown in Table 14, the quantity ratio between the JAK2 primer Fwt and the JAK2 primer Fmt was changed, thereby testing influence of the quantity ratio on the detection sensitivity of the mutated plasmid.

Table 15 shows the conditions for the PCR and the Tm analysis. Additionally, excitation wavelength and detection wavelength in the Tm analysis were 520 to 555 nm and 585 to 700 nm, respectively.

TABLE 13

In 50 μl of the PCR reaction solution:

1 × reaction buffer
1.25 U Taq polymerase
1.5 mmol/L MgCl₂
0.2 mmol/L dNTP

TABLE 13-continued

In 50 μl of the PCR reaction solution:

0.25 μmol/L JAK2 primer Fwt (Table 2)
1 μmol/L JAK2 primer R (Table 2)
0.2 μmol/L JAK2 mt probe (Table 2)

*The concentration of JAK2 primer Fmt (Table 2) is referred to in Table 14.

TABLE 14

| primer quantity ratio: Fwt/Fmt | 0.5 time by mole | 1 time by mole | 2 times by mole |
|---|---|---|---|
| Concentration of JAK2 primer Fmt in PCR reaction solution (μmol/L) | 0.5 | 0.25 | 0.125 |

TABLE 15

PCR conditions/Tm analysis conditions

Figure 4:
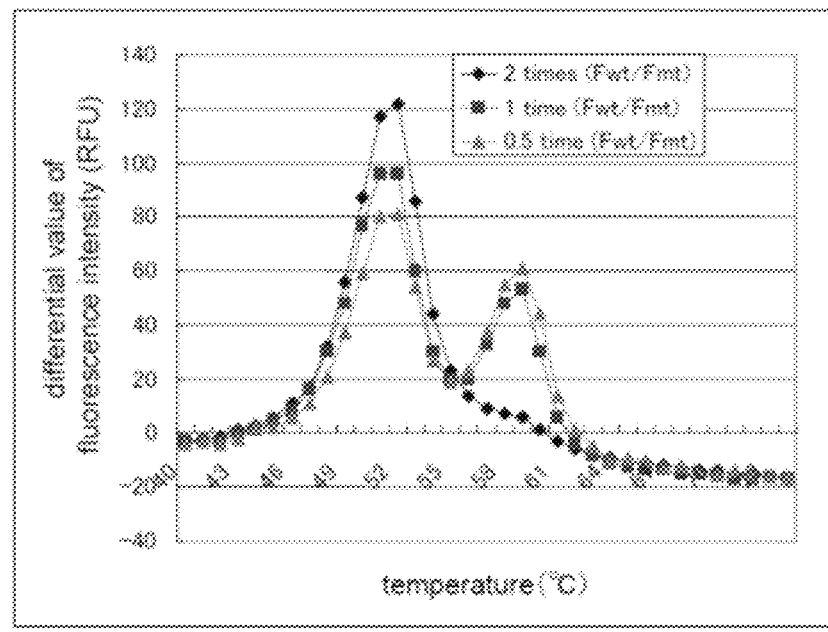
FIG. 4 is a view showing the influence of the quantity ratio between a first primer and a second primer on the detection sensitivity of a mutated plasmid (the target polynucleotide).

95° C., 60 seconds
↓
(95° C., 1 second → 60° C., 15 seconds) × 50 cycles
↓
95° C., 1 second
↓
40° C., 60 seconds
↓
Tm analysis: 40° C. → 75° C., 1° C./3 seconds FIG. 4 shows the results of the PCR and the Tm analysis. In FIG. 4, the vertical axis represents the differential values of fluorescence intensity (Relative Fluorescence Units (RFU)) and the horizontal axis represents temperatures (° C.). The peak seen at around 51° C. indicates a peak resulted from the presence of the wild-type plasmid, and the peak seen at around 59° C. indicates a peak resulted from the presence of the mutated plasmid.

As shown in FIG. 4, the peak resulted from the presence of the mutated plasmid became larger, as the quantity of the JAK2 primer Fwt with respect to the JAK2 primer Fmt (Fwt/Fmt) was decreased from 2 times by mole to 0.5 times by mole.

This indicated the regularity that as the value of (Fwt/Fmt) becomes smaller, the amplification efficiency of the mutated plasmid increases.

The results obtained in Example 3 and Example 4 showed that changing the quantity ratio between a plurality of primers having an allele-specific nucleotide (the first primer and the second primer) allows for an increase in the amplification efficiency of a DNA having a particular allele-specific nucleotide.

Example 5

The samples were prepared by mixing the kit Wt plasmid and the kit D617V plasmid prepared in Example 3 in the ratio of 1:0, 99:1, 97:3, and 9:1, and the prepared samples were defined as Wt, Mt1%, Mt3%, and Mt10%, respectively. By using 50 μl of the PCR reaction solutions containing 10⁴ copies of these samples respectively and each component of the PCR reaction shown below at the concentrations shown below, PCR and Tm analysis were performed by using a full-automated SNP analyzer (trade name: i-densy (registered trademark) from Arkray Inc.).

In 50 μl of the PCR reaction solution:
- 1× reaction buffer
- 1.25 U Taq polymerase
- 1.5 mmol/L MgCl$_2$
- 0.2 mmol/L dNTP
- 0.25 μmol/L kit primer Fwt (Table 10)
- 0.25 μmol/L kit primer Fmt (Table 10)
- 0.2 μmol/L kit mt probe (Table 10)

*The concentration of kit primer R (Table 10) is referred to in Table 16.

TABLE 16

| primer quantity ratio: R/(Fwt + Fmt) | 1 time by mole | 2 times by mole | 4 times by mole | 8 times by mole | 16 times by mole |
|---|---|---|---|---|---|
| Concentration of kit primer R in PCR reaction solution (μmol/L) | 0.5 | 1 | 2 | 4 | 8 |

The other reaction conditions were the same as those in Example 3.

FIG. 5 shows the results of the PCR and the Tm analysis. In FIG. 5, the vertical axis represents the differential values of fluorescence intensity (Relative Fluorescence Units (RFU)) and the horizontal axis represents temperatures (° C.). The peak seen at around 48° C. indicates a peak resulted from the presence of the wild-type plasmid, and the peak seen at around 56° C. indicates a peak resulted from the presence of the mutated plasmid.

Figure 5A:
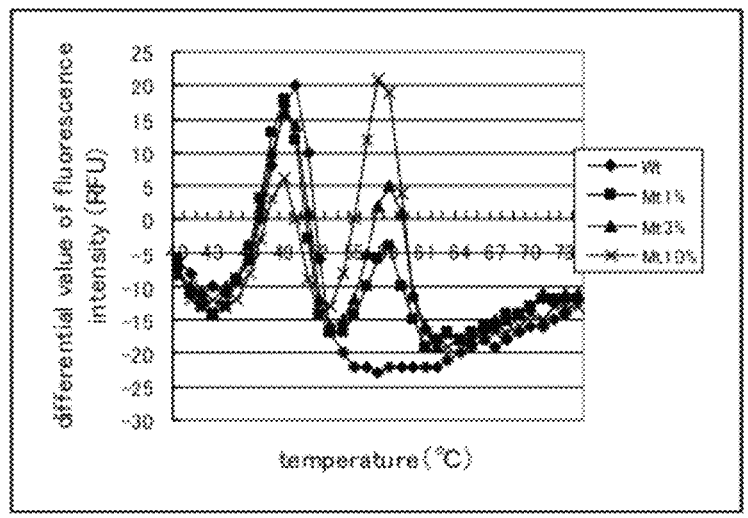
FIG. 5A is a view showing the influence of the quantity ratio between the total quantity of a first primer and a second primer and the quantity of a third primer on the detection sensitivity of a mutated plasmid (a target polynucleotide); the quantity ratio (R/(Fwt+Fmt)) is 1 time by mole.
Figure 5B:
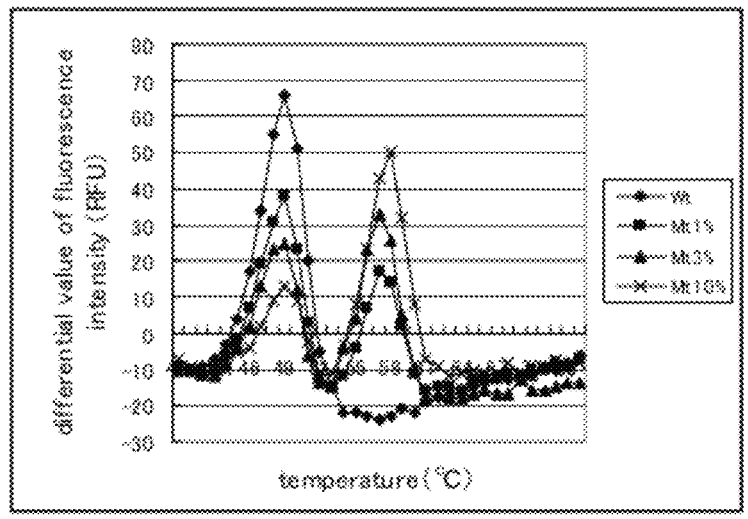
FIG. 5B is a view showing the influence of the quantity ratio between the total quantity of a first primer and a second primer and the quantity of a third primer on the detection sensitivity of a mutated plasmid (a target polynucleotide); the quantity ratio (R/(Fwt+Fmt)) is 2 times by mole.
Figure 5C:
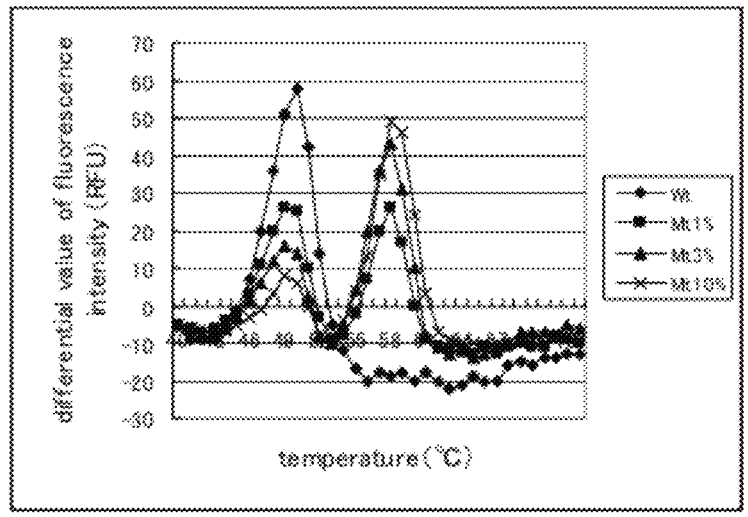
FIG. 5C is a view showing the influence of the quantity ratio between the total quantity of a first primer and a second primer and the quantity of a third primer on the detection sensitivity of a mutated plasmid (a target polynucleotide); the quantity ratio (R/(Fwt+Fmt)) is 4 times by mole.
Figure 5D:
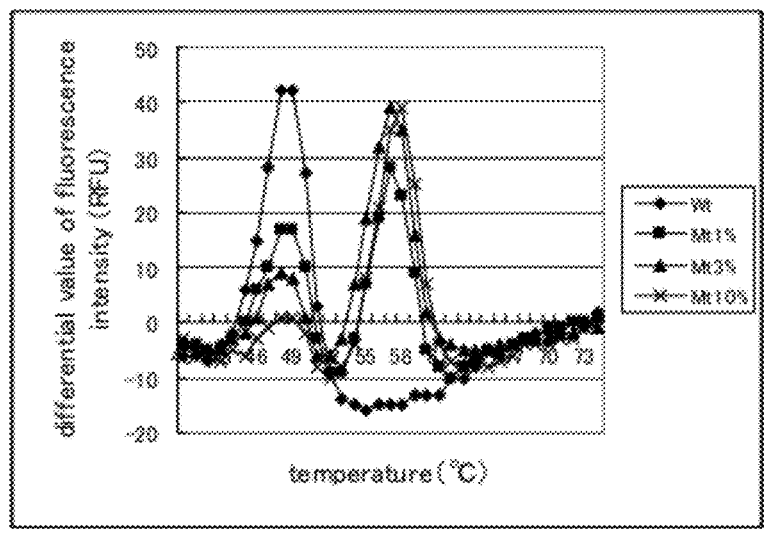
FIG. 5D is a view showing the influence of the quantity ratio between the total quantity of a first primer and a second primer and the quantity of a third primer on the detection sensitivity of a mutated plasmid (a target polynucleotide); the quantity ratio (R/(Fwt+Fmt)) is 8 times by mole.
Figure 5E:
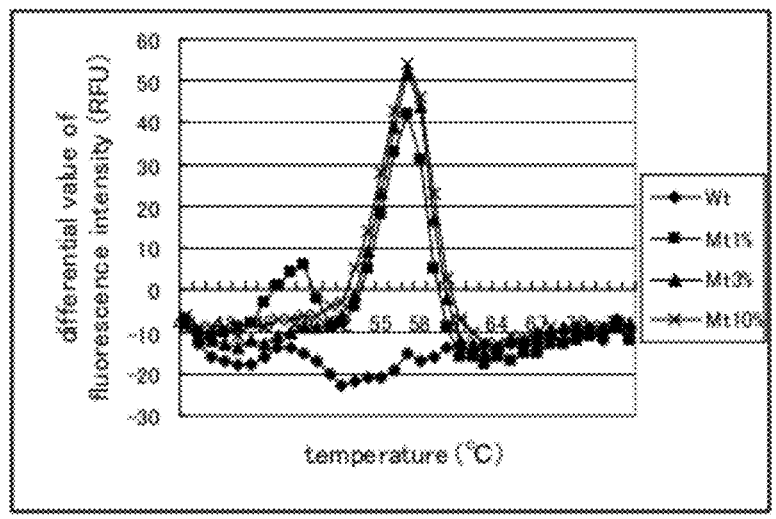
FIG. 5E is a view showing the influence of the quantity ratio between the total quantity of a first primer and a second primer and the quantity of a third primer on the detection sensitivity of a mutated plasmid (a target polynucleotide); the quantity ratio (R/(Fwt+Fmt)) is 16 times by mole.

As shown in FIG. 5A to 5E, the peak resulted from the presence of the mutated plasmid became larger, as the quantity of the kit primer R with respect to the total quantity of the kit primer Fwt and the kit primer Fmt (R/(Fwt+Fmt)) was increased to 1 time by mole (FIG. 5A), 2 times by mole (FIG. 5B), 4 times by mole (FIG. 5C), 8 times by mole (FIG. 5D), and 16 times by mole (FIG. 5E). However, in the case of the value of (R/(Fwt+Fmt)) was 16 times by mole, the peak resulted from the presence of the wild-type plasmid was hardly detected.

This indicated the regularity that as the value of (R/(Fwt+Fmt)) becomes larger, the amplification efficiency of the mutated plasmid increases. However, it was also indicated that in the case of the value of (R/(Fwt+Fmt)) was 16 times by mole, the peak resulted from the presence of the wild-type plasmid was hardly detected, and thus, this was hard to be distinguished from a poor reaction.

Example 6

The samples were prepared by mixing the JAK2 Wt plasmid and the JAK2 V617F plasmid prepared in Example 1 in the ratio of 1:0, 99:1, 97:3, and 9:1, and the prepared samples were defined as Wt, Mt1%, Mt3%, and Mt10%, respectively. By using 50 μl of the PCR reaction solutions containing 10$^4$ copies of these samples respectively and each component of the PCR reaction shown below at the concentrations shown below, PCR and Tm analysis were performed by using a full-automated SNP analyzer (trade name: i-densy (registered trademark) from Arkray Inc.).

In 50 μl of the PCR reaction solution:
- 1× reaction buffer
- 1.25 U Taq polymerase
- 1.5 mmol/L MgCl$_2$
- 0.2 mmol/L dNTP
- 0.25 μmol/L JAK2 primer Fwt (Table 2)
- 0.25 μmol/L JAK2 primer Fmt (Table 2)
- 0.2 μmol/L JAK2 ml probe (Table 2)

*The concentration of JAK2 primer R (Table 2) is referred to in Table 17.

TABLE 17

| primer quantity ratio: R/(Fwt + Fmt) | 1 time by mole | 2 times by mole | 4 times by mole | 8 times by mole | 16 times by mole |
|---|---|---|---|---|---|
| Concentration of JAK2 primer R in PCR reaction solution (μmol/L) | 0.5 | 1 | 2 | 4 | 8 |

The other reaction conditions were the same as those in Example 1.

FIG. 6 shows the results of the PCR and the Tm analysis. In FIG. 6, the vertical axis represents the differential values of fluorescence intensity (Relative Fluorescence Units (RFU)) and the horizontal axis represents temperatures (° C.). The peak seen at around 51° C. indicates a peak resulted from the presence of the wild-type plasmid, and the peak seen at around 59° C. indicates a peak resulted from the presence of the mutated plasmid.

Figure 6A:
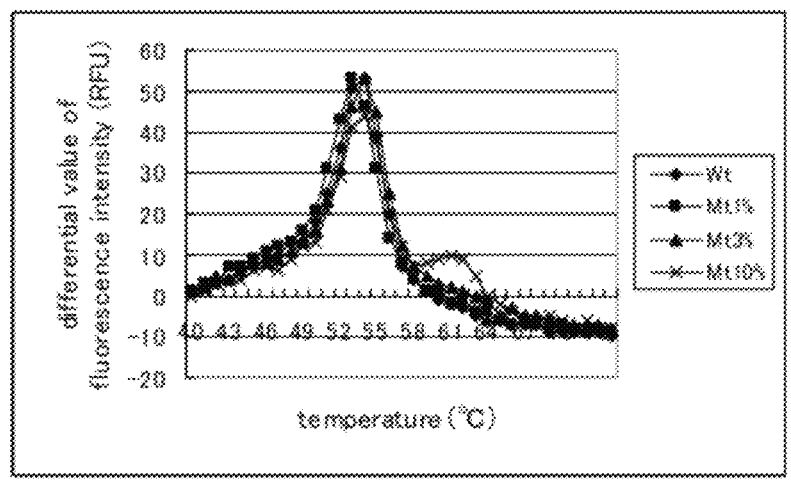
FIG. 6A is a view showing the influence of the quantity ratio between the total quantity of a first primer and a second primer and the quantity of a third primer on the detection sensitivity of a mutated plasmid (a target polynucleotide); the quantity ratio (R/(Fwt+Fmt)) is 1 time by mole.
Figure 6B:
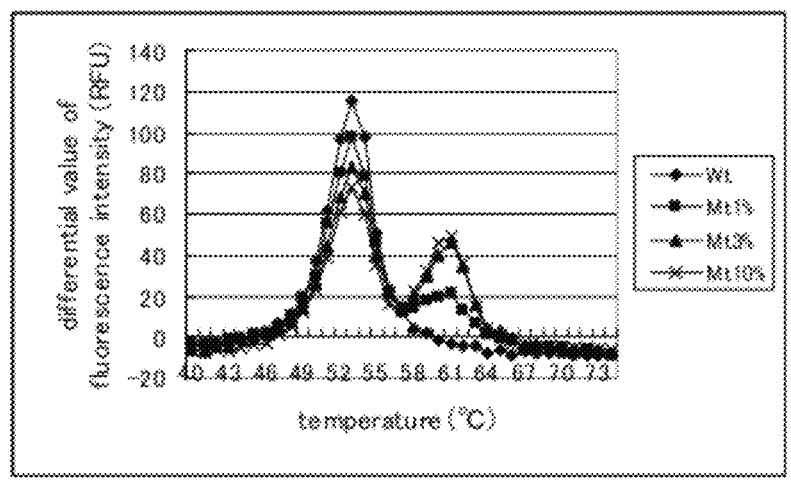
FIG. 6B is a view showing the influence of the quantity ratio between the total quantity of a first primer and a second primer and the quantity of a third primer on the detection sensitivity of a mutated plasmid (a target polynucleotide); the quantity ratio (R/(Fwt+Fmt)) is 2 times by mole.
Figure 6C:
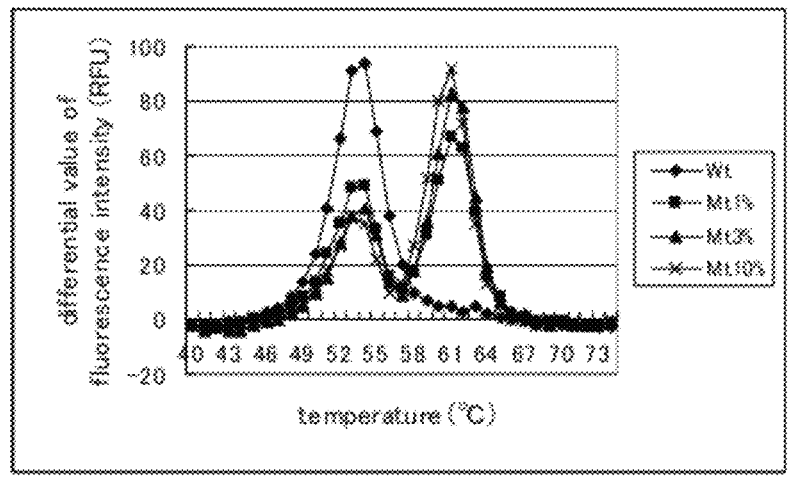
FIG. 6C is a view showing the influence of the quantity ratio between the total quantity of a first primer and a second primer and the quantity of a third primer on the detection sensitivity of a mutated plasmid (a target polynucleotide); the quantity ratio (R/(Fwt+Fmt)) is 4 times by mole.
Figure 6D:
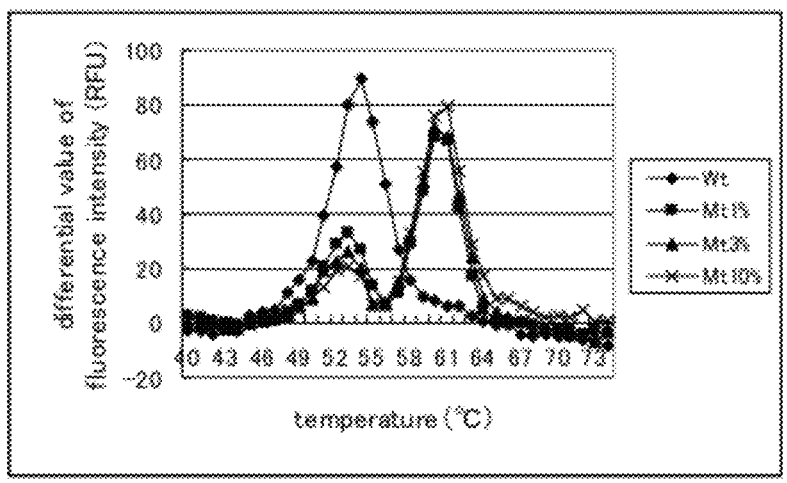
FIG. 6D is a view showing the influence of the quantity ratio between the total quantity of a first primer and a second primer and the quantity of a third primer on the detection sensitivity of a mutated plasmid (a target polynucleotide); the quantity ratio (R/(Fwt+Fmt)) is 8 times by mole.
Figure 6E:
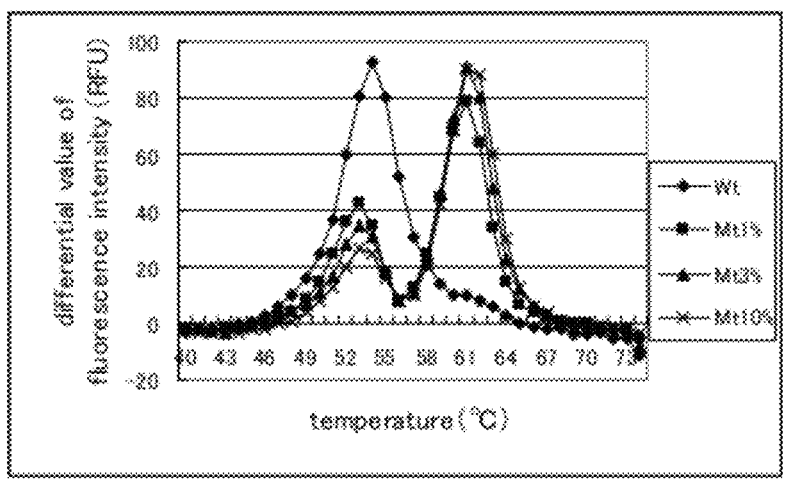
FIG. 6E is a view showing the influence of the quantity ratio between the total quantity of a first primer and a second primer and the quantity of a third primer on the detection sensitivity of a mutated plasmid (a target polynucleotide); the quantity ratio (R/(Fwt+Fmt)) is 16 times by mole.

As shown in FIG. 6A to 6E, the peak resulted from the presence of the mutated plasmid became larger, as the quantity of the JAK2 primer R with respect to the total quantity of the JAK2 primer Fwt and the JAK2 primer Fmt (R/(Fwt+Fmt)) was increased to 1 time by mole (FIG. 6A), 2 times by mole (FIG. 6B), 4 times by mole (FIG. 6C), 8 times by mole (FIG. 6D), and 16 times by mole (FIG. 6E).

This indicated the regularity that as the value of (R/(Fwt+Fmt)) becomes larger, the amplification efficiency of the mutated plasmid increases.

Example 7

By using 50 μl of the PCR reaction solutions containing 10$^4$ copies of the samples of Wt, Mt1%, Mt3%, and Mt10% prepared in Example 5 respectively and each component of the PCR reaction shown below at the concentrations shown below, PCR and Tm analysis were performed by using a full-automated SNP analyzer (trade name: i-densy (registered trademark) from Arkray Inc.).

In 50 μl of the PCR reaction solution:
- 1× reaction buffer
- 1.25 U Taq polymerase
- 1.5 mmol/L MgCl$_2$
- 0.2 mmol/L dNTP
- 1 μmol/L kit primer R (Table 10)
- 0.2 μmol/L kit mt probe (Table 10)

*The concentrations of kit primer Fwt (Table 10) and kit primer Fmt (Table 10) are referred to in Table 18.

TABLE 18

| primer quantity ratio: Fwt/Fmt | ⅓ time by mole | ½ time by mole | 1 time by mole | 2 times by mole | 3 times by mole |
|---|---|---|---|---|---|
| Concentration of kit primer Fwt in PCR reaction solution (μmol/L) | 0.125 | 0.166 | 0.25 | 0.334 | 0.375 |
| Concentration of kit primer Fmt in PCR reaction solution (μmol/L) | 0.375 | 0.334 | 0.25 | 0.166 | 0.125 |

The other reaction conditions were the same as those in Example 3.

FIG. 7 shows the results of the PCR and the Tm analysis. In FIG. 7, the vertical axis represents the differential values of fluorescence intensity (Relative Fluorescence Units (RFU)) and the horizontal axis represents temperatures (° C.). The peak seen at around 48° C. indicates a peak resulted from the presence of the wild-type plasmid, and the peak seen at around 56° C. indicates a peak resulted from the presence of the mutated plasmid.

Figure 7A:
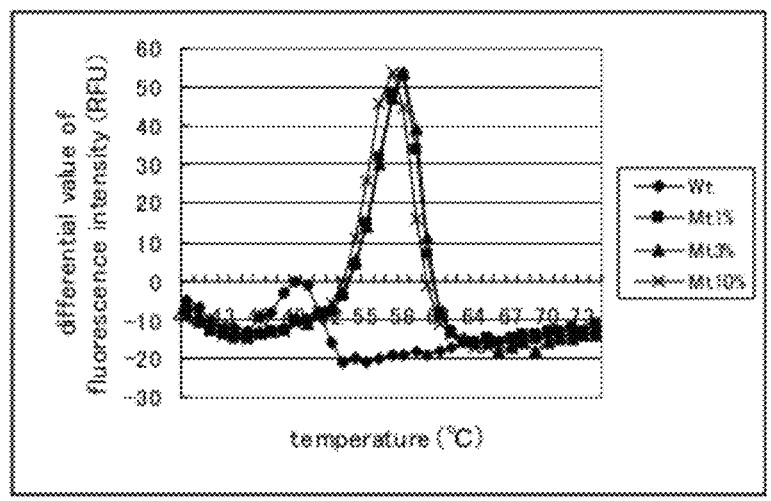
FIG. 7A is a view showing the influence of the quantity ratio between a first primer and a second primer on the detection sensitivity of a mutated plasmid (a target polynucleotide); the quantity ratio (Fwt/Fmt) is 1/3 time by mole.
Figure 7B:
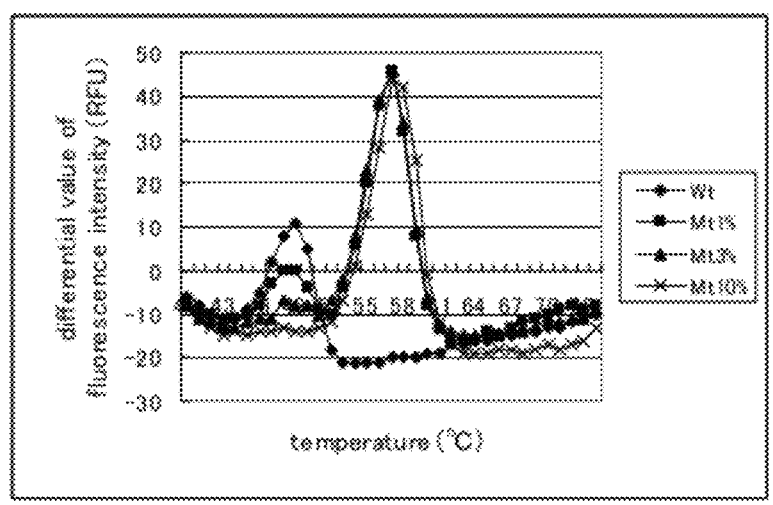
FIG. 7B is a view showing the influence of the quantity ratio between a first primer and a second primer on the detection sensitivity of a mutated plasmid (a target polynucleotide); the quantity ratio (Fwt/Fmt) is 1/2 time by mole.
Figure 7C:
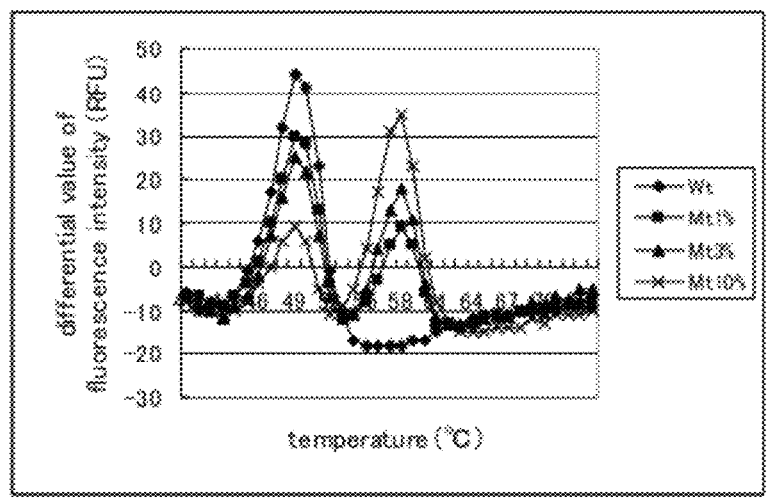
FIG. 7C is a view showing the influence of the quantity ratio between a first primer and a second primer on the detection sensitivity of a mutated plasmid (a target polynucleotide); the quantity ratio (Fwt/Fmt) is 1 time by mole.
Figure 7D:
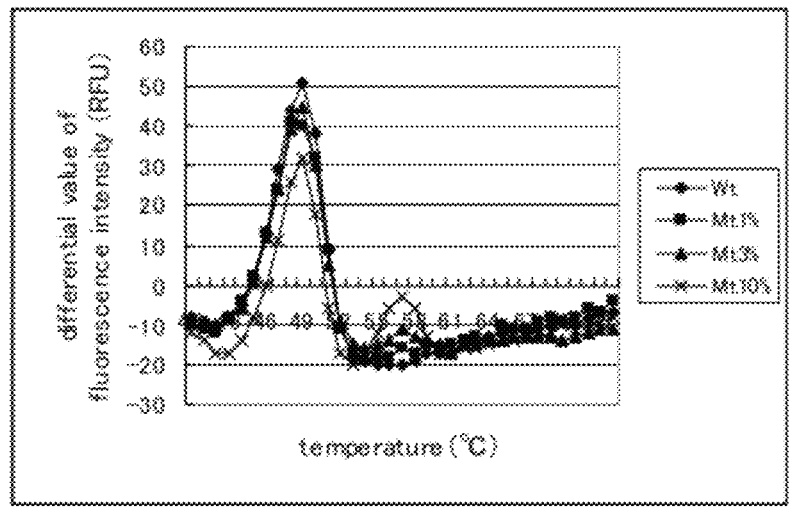
FIG. 7D is a view showing the influence of the quantity ratio between a first primer and a second primer on the detection sensitivity of a mutated plasmid (a target polynucleotide); the quantity ratio (Fwt/Fmt) is 2 times by mole.
Figure 7E:
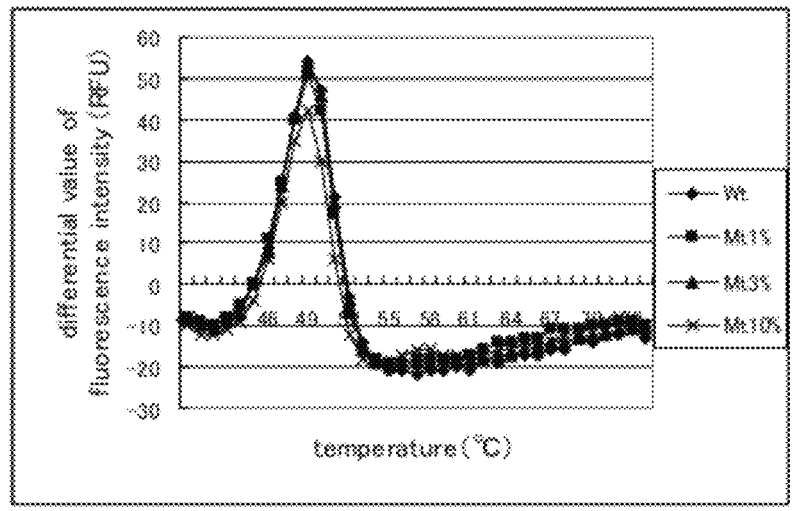
FIG. 7E is a view showing the influence of the quantity ratio between a first primer and a second primer on the detection sensitivity of a mutated plasmid (a target polynucleotide); the quantity ratio (Fwt/Fmt) is 3 times by mole.
Figure 8A:
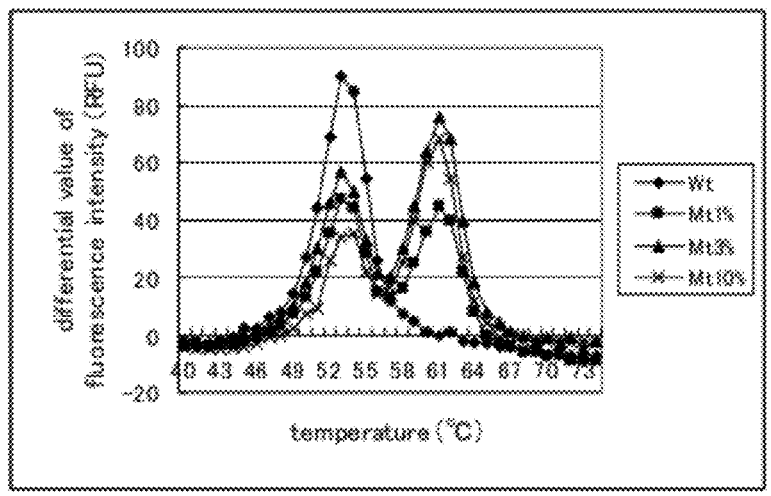
FIG. 8A is a view showing the influence of the quantity ratio between a first primer and a second primer on the detection sensitivity of a mutated plasmid (a target polynucleotide); the quantity ratio (Fwt/Fmt) is 1/4 time by mole.
Figure 8B:
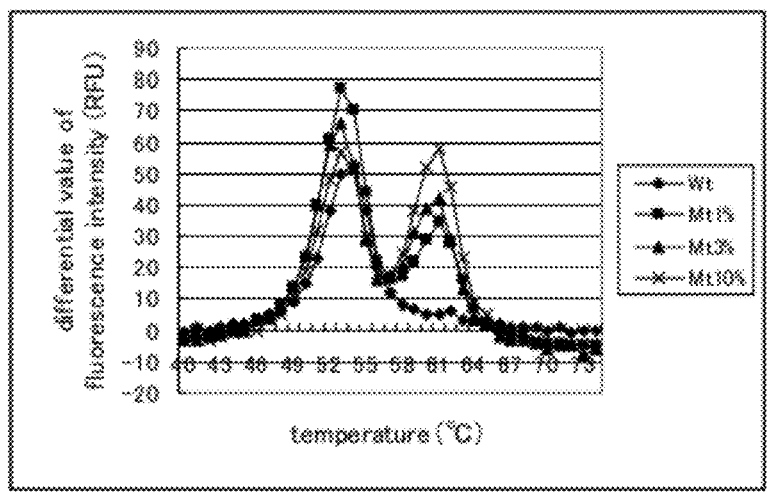
FIG. 8B is a view showing the influence of the quantity ratio between a first primer and a second primer on the detection sensitivity of a mutated plasmid (a target polynucleotide); the quantity ratio (Fwt/Fmt) is 1/2 time by mole.
Figure 8C:
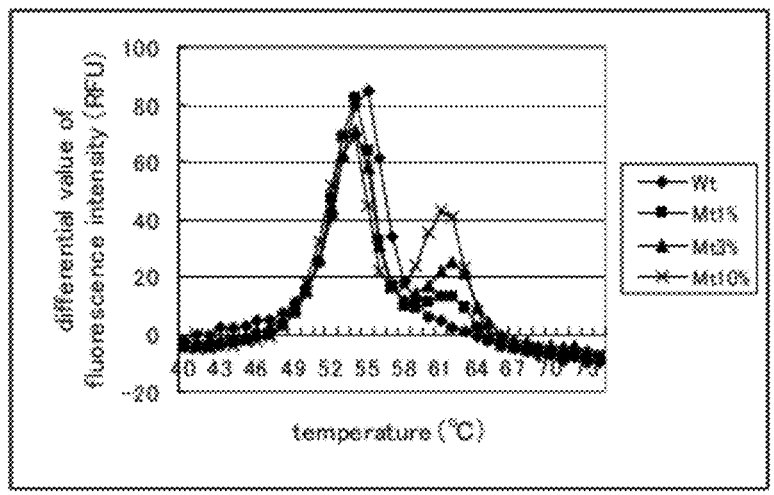
FIG. 8C is a view showing the influence of the quantity ratio between a first primer and a second primer on the detection sensitivity of a mutated plasmid (a target polynucleotide); the quantity ratio (Fwt/Fmt) is 1 time by mole.
Figure 8D:
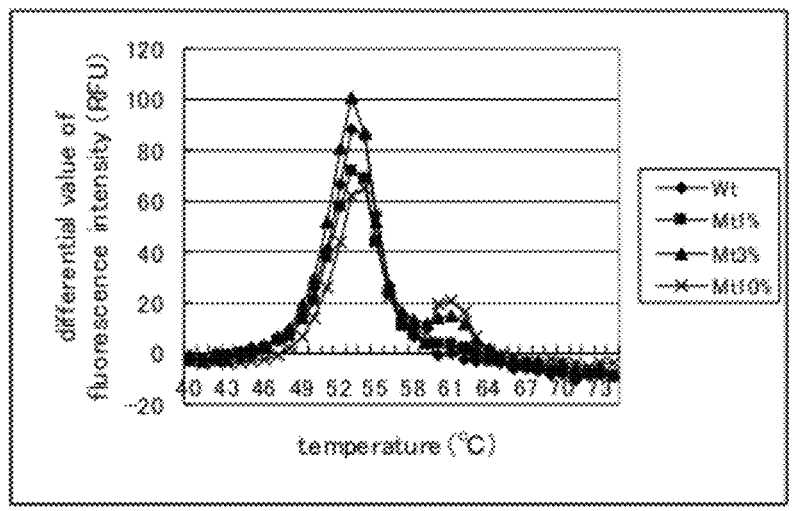
FIG. 8D is a view showing the influence of the quantity ratio between a first primer and a second primer on the detection sensitivity of a mutated plasmid (a target polynucleotide); the quantity ratio (Fwt/Fmt) is 2 times by mole.
Figure 8E:
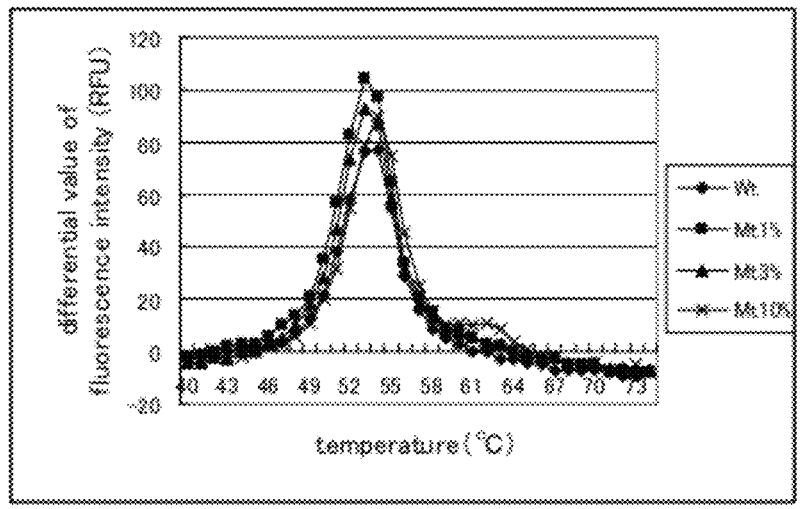
FIG. 8E is a view showing the influence of the quantity ratio between a first primer and a second primer on the detection sensitivity of a mutated plasmid (a target polynucleotide); the quantity ratio (Fwt/Fmt) is 3 times by mole.

As shown in FIG. 7A to 7E, the peak resulted from the presence of the mutated plasmid became larger, as the quantity of the kit primer Fwt with respect to the quantity of the kit primer Fmt (Fwt/Fmt) was decreased to 3 times by mole (FIG. 7E), 2 times by mole (FIG. 7D), 1 time by mole (FIG. 7C), 1/2 time by mole (FIG. 7B), and 1/3 time by mole (FIG. 7A).

This indicated the regularity that as the value of (Fwt/Fmt) becomes smaller, the amplification efficiency of the mutated plasmid increases. Also, it was indicated that in the case of the value of (Fwt/Fmt) was 3 times by mole, the peak resulted from the presence of the wild-type plasmid was hardly detected in any of the samples.

Example 8

By using 50 μl of the PCR reaction solutions containing $10^4$ copies of the samples of Wt, Mt1%, Mt3%, and Mt10% prepared in Example 6 respectively and each component of the PCR reaction shown below at the concentrations shown below, PCR and Tm analysis were performed by using a full-automated SNP analyzer (trade name: i-densy (registered trademark) from Arkray Inc.).

In 50 μl of the PCR reaction solution:
- 1× reaction buffer
- 1.25 U Taq polymerase
- 1.5 mmol/L $MgCl_2$
- 0.2 mmol/L dNTP
- 1 μmol/L JAK2 primer R (Table 2)
- 0.2 μmol/L JAK2 mt probe (Table 2)

*The concentrations of JAK2 primer Fwt (Table 2) and JAK2 primer Fmt (Table 2) are referred to in Table 19.

TABLE 19

| primer quantity ratio: Fwt/Fmt | 1/4 time by mole | 1/2 time by mole | 1 time by mole | 2 times by mole | 3 times by mole |
|---|---|---|---|---|---|
| Concentration of JAK2 primer Fwt in PCR reaction solution (μmol/L) | 0.1 | 0.166 | 0.25 | 0.334 | 0.375 |
| Concentration of JAK2 primer Fmt in PCR reaction solution (μmol/L) | 0.4 | 0.334 | 0.25 | 0.166 | 0.125 |

The other reaction conditions were the same as those in Example 1.

FIG. 8 shows the results of the PCR and the Tm analysis. In FIG. 8, the vertical axis represents the differential values of fluorescence intensity (Relative Fluorescence Units (RFU)) and the horizontal axis represents temperatures (° C.). The peak seen at around 51° C. indicates a peak resulted from the presence of the wild-type plasmid, and the peak seen at around 59° C. indicates a peak resulted from the presence of the mutated plasmid.

As shown in FIG. 8A to 8E, the peak resulted from the presence of the mutated plasmid became larger, as the quantity of the JAK2 primer Fwt with respect to the quantity of the JAK2 primer Fmt (Fwt/Fmt) was decreased to 3 times by mole (FIG. 7E), 2 times by mole (FIG. 7D), 1 time by mole (FIG. 7C), 1/2 time by mole (FIG. 7B), and 1/4 time by mole (FIG. 7A).

This indicated the regularity that as the value of (Fwt/Fmt) becomes smaller, the amplification efficiency of the mutated plasmid increases. Also, it was indicated that in the case of the value of (Fwt/Fmt) was 3 times by mole, the peak resulted from the presence of the wild-type plasmid was hardly detected in any of the samples.

INDUSTRIAL APPLICABILITY

The present invention provides a tool for investigating clinically valuable detection sensitivity regarding mutations of various genes.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method of adjusting the amplification efficiency of a target polynucleotide in the amplification of the target polynucleotide by PCR using primers (i) to (iii) below in the same amplification, the method comprising
adjusting the amplification efficiency of the target polynucleotide by changing the quantity ratio of the primers (i) to (iii) below:
(i) a first primer which is able to be base-paired with the target polynucleotide;
(ii) a second primer which is able to be base-paired with the target polynucleotide at the same region with which the first primer is configured to hybridize to and from which extension reaction by PCR occurs less as compared to the first primer; and
(iii) a third primer designed to allow for the amplification of the target polynucleotide in pairs with the first primer,
wherein the Tm value of the first primer is higher than the Tm value of the second primer, and
the adjusting comprises changing the quantity of the third primer with respect to the total quantity of the first primer and the second primer.

2. The method according to claim 1, wherein the target polynucleotide comprises a single nucleotide polymorphism (SNP) site; the first and second primers hybridize with a region comprising the SNP site; the first primer has a nucleotide corresponding to a first allele-specific nucleotide of the SNP site at any of the first to fifth positions from the 3' end; and the second primer has a nucleotide corresponding to a second allele-specific nucleotide of the SNP site at any of the first to fifth positions from the 3' end.

3. The method according to claim 1, wherein the amplification efficiency of the target polynucleotide is increased by increasing the quantity of the third primer with respect to the total quantity of the first primer and the second primer.

4. The method according to claim 1, wherein the amplification efficiency of the target polynucleotide is decreased by decreasing the quantity of the third primer with respect to the total quantity of the first primer and the second primer.

5. The method according to claim 3, wherein the amplification efficiency of the target polynucleotide comprising the first allele-specific nucleotides increased by increasing the quantity of the third primer with respect to the total quantity of the first primer and the second primer to more than 1 time by mole.

6. The method according to claim 5, wherein the amplification efficiency of the target polynucleotide is increased by increasing the quantity of the third primer with respect to the total quantity of the first primer and the second primer to more than 2 times by mole.

7. The method according to claim 1, wherein the amplification efficiency of the target polynucleotide is increased by increasing the quantity of the first primer with respect to the quantity of the second primer.

8. A method of adjusting the detection efficiency of a target polynucleotide in the detection of the target polynucleotide using an amplification product obtained by amplifying the target polynucleotide by PCR using the primers (i) to (iii), the method comprising
adjusting the detection efficiency of the target polynucleotide by changing the amplification efficiency of the target polynucleotide using the method according to claim 1.

9. A method of detecting a target polynucleotide, comprising:
adjusting the detection efficiency of the target polynucleotide by the method according to claim 8;
performing PCR using the primers (i) to (iii) with a quantity ratio that achieves the adjusted detection efficiency; and
detecting the target polynucleotide in an obtained PCR amplification product.

10. A method of testing the possibility of a disease due to the presence of a mutation, comprising detecting the presence or absence of a mutation in a gene derived from a subject by using the detection method according to claim 9, wherein the presence of the mutation is indicative of increased risk of the disease.

11. A method of predicting the efficacy of a medicine, comprising:
detecting the presence or absence of a mutation in a gene derived from a subject by using the detection method according to claim 9;
comparing an obtained detection result with the relationship between the presence or absence of the mutation and the efficacy of a specific medicine; and
thereby predicting the efficacy of the specific medicine on the subject.

12. A method of producing a primer set, comprising:
adjusting the amplification efficiency of a target polynucleotide using the method according to claim 1; and
formulating the primers (i) to (iii) in a quantity ratio that achieves the adjusted amplification efficiency.

13. The method according to claim 1, wherein the target polynucleotide has a sequence from a gene selected from the group consisting of JAK2 gene, abl gene, and kit gene.

14. The method according to claim 13, wherein
the target polynucleotide has a sequence from the JAK2 gene;

each of the first and second primers comprises nucleotide sequences of SEQ ID NO: 2 or 3; and the third primer comprises a nucleotide sequence of SEQ ID NO: 4.

15. The method according to claim 13, wherein the target polynucleotide has a sequence from the abl gene;

each of the first and second primers comprises nucleotide sequences of SEQ ID NO: 8 or 9; and the third primer comprises a nucleotide sequence of SEQ ID NO: 7.

16. The method according to claim 13, wherein the target polynucleotide has a sequence from the kit gene;

each of the first and second primers comprises nucleotide sequences of SEQ ID NO: 12 or 13; and the third primer comprises a nucleotide sequence of SEQ ID NO: 14.

17. The method according to claim 1, wherein the adjusting step comprises increasing an amount of the first, second, or third primer.

\* \* \* \* \*

SEQUENCE LISTING

<160> NUMBER OF SEQ ID NOS: 15

<210> SEQ ID NO 1
<211> LENGTH: 300
<212> TYPE: DNA
<213> ORGANISM: Homo sapiens

<400> SEQUENCE: 1

```
ggcagagaga attttctgaa ctatttatgg acaacagtca aacaacaatt ctttgtactt      60
ttttttttcc ttagtctttc tttgaagcag caagtatgat gagcaagctt tctcacaagc     120
atttggtttt aaattatgga gtatgtgtct gtggagacga gagtaagtaa aactacaggc     180
tttctaatgc ctttctcaga gcatctgttt ttgtttatat agaaaattca gtttcaggat     240
cacagctagg tgtcagtgta aactataatt taacaggagt taagtatttt tgaaactgaa     300
```

```
<210> SEQ ID NO 2
<211> LENGTH: 32
<212> TYPE: DNA
<213> ORGANISM: Artificial Sequence
<220> FEATURE:
<223> OTHER INFORMATION: Artificially synthesized primer

<400> SEQUENCE: 2
tgctcatttg gttttaaatt atggagtatg tg                                    32

<210> SEQ ID NO 3
<211> LENGTH: 34
<212> TYPE: DNA
<213> ORGANISM: Artificial Sequence
<220> FEATURE:
<223> OTHER INFORMATION: Artificially synthesized primer

<400> SEQUENCE: 3
gtctggcatt tggttttaaa ttatggagta tgtt                                  34

<210> SEQ ID NO 4
<211> LENGTH: 27
<212> TYPE: DNA
<213> ORGANISM: Artificial Sequence
<220> FEATURE:
<223> OTHER INFORMATION: Artificially synthesized primer

<400> SEQUENCE: 4
gctctgagaa aggcattaga aagcctg                                          27

<210> SEQ ID NO 5
<211> LENGTH: 19
<212> TYPE: DNA
<213> ORGANISM: Artificial Sequence
<220> FEATURE:
<223> OTHER INFORMATION: Artificially synthesized probe

<400> SEQUENCE: 5
agtatgtttc tgtggagac                                                   19

<210> SEQ ID NO 6
<211> LENGTH: 120
<212> TYPE: DNA
<213> ORGANISM: Homo sapiens

<400> SEQUENCE: 6
gcggagccac gtgttgaagt cctcgttgtc ttgttggcag gggtctgcac ccggagcccc      60 cgttctata tcatcactga gttcatgacc tacgggaacc tcctggacta cctgagggag      120

<210> SEQ ID NO 7
<211> LENGTH: 33
<212> TYPE: DNA
<213> ORGANISM: Artificial Sequence
<220> FEATURE:
<223> OTHER INFORMATION: Artificially synthesized primer

<400> SEQUENCE: 7
ggacggacgg accgtcctcg ttgtcttgtt ggc                                   33

<210> SEQ ID NO 8
<211> LENGTH: 27
<212> TYPE: DNA
<213> ORGANISM: Artificial Sequence
<220> FEATURE:
<223> OTHER INFORMATION: Artificially synthesized primer
```

<400> SEQUENCE: 8
ctacgttccc gtaggtcatg aactcag                              27

<210> SEQ ID NO 9
<211> LENGTH: 30
<212> TYPE: DNA
<213> ORGANISM: Artificial Sequence
<220> FEATURE:
<223> OTHER INFORMATION: Artificially synthesized primer

<400> SEQUENCE: 9
tgctcaggtt cccgtaggtc atgaactcaa                           30

<210> SEQ ID NO 10
<211> LENGTH: 20
<212> TYPE: DNA
<213> ORGANISM: Artificial Sequence
<220> FEATURE:
<223> OTHER INFORMATION: Artificially synthesized probe

<400> SEQUENCE: 10
ctcaatgatg atatagaacg                                      20

<210> SEQ ID NO 11
<211> LENGTH: 360
<212> TYPE: DNA
<213> ORGANISM: Homo sapiens

<400> SEQUENCE: 11
tttttggtgt actgaatact ttaaaacaaa agtattggat tttttataat ataagcaaca    60
ctatagtatt aaaaagttag ttttcactct ttacaagtta aaatgaattt aaatggtttt   120
cttttctcct ccaacctaat agtgtattca cagagacttg gcagccagaa atatcctcct   180
tactcatggt cggatcacaa agatttgtga ttttggtcta gccagagaca tcaagaatga   240
ttctaattat gtggttaaag gaaacgtgag tacccattct ctgcttgaca gtcctgcaaa   300
ggatttttag tttcaacttt cgataaaaat tgtttcctgt gattttcata atgtaaatcc   360

<210> SEQ ID NO 12
<211> LENGTH: 19
<212> TYPE: DNA
<213> ORGANISM: Artificial Sequence
<220> FEATURE:
<223> OTHER INFORMATION: Artificially synthesized primer

<400> SEQUENCE: 12
attttggtct agccagaga                                       19

<210> SEQ ID NO 13
<211> LENGTH: 21
<212> TYPE: DNA
<213> ORGANISM: Artificial Sequence
<220> FEATURE:
<223> OTHER INFORMATION: Artificially synthesized primer

<400> SEQUENCE: 13
tgattttggt ctagccagag t                                    21

<210> SEQ ID NO 14
<211> LENGTH: 20
<212> TYPE: DNA
<213> ORGANISM: Artificial Sequence
<220> FEATURE:
<223> OTHER INFORMATION: Artificially synthesized primer

```
<400> SEQUENCE: 14
aaatcctttg caggactgtc                                              20

<210> SEQ ID NO 15
<211> LENGTH: 18
<212> TYPE: DNA
<213> ORGANISM: Artificial Sequence
<220> FEATURE:
<223> OTHER INFORMATION: Artificially synthesized probe

<400> SEQUENCE: 15
ccagagtcat caagaatg                                                18
```